(12) United States Patent
Baur et al.

(10) Patent No.: US 9,510,589 B2
(45) Date of Patent: Dec. 6, 2016

(54) USE AND AGROCHEMICAL COMPOSITION OF CARBOXYLIC ACID DIBUTYLAMIDES

(75) Inventors: Peter Baur, Schondorf (DE); Martin Steinbeck, Cologne (DE); Ingo Wetcholowsky, Langenfeld (DE); Thomas Auler, Bergisch Gladbach (DE); Rolf Pontzen, Leichlingen (DE); Alison Daniels, Gt Sampford (GB)

(73) Assignee: BAYER INTELLECTUAL PROPERTY GMBH, Monheim (DE)

( * ) Notice: Subject to any disclaimer, the term of this patent is extended or adjusted under 35 U.S.C. 154(b) by 70 days.

(21) Appl. No.: 14/232,200

(22) PCT Filed: Aug. 10, 2012

(86) PCT No.: PCT/EP2012/065685
§ 371 (c)(1),
(2), (4) Date: May 9, 2014

(87) PCT Pub. No.: WO2013/021045
PCT Pub. Date: Feb. 14, 2013

(65) Prior Publication Data
US 2014/0256716 A1    Sep. 11, 2014

Related U.S. Application Data

(60) Provisional application No. 61/522,798, filed on Aug. 12, 2011.

(30) Foreign Application Priority Data

Aug. 11, 2011 (EP) .................................... 11177196

(51) Int. Cl.
*A01N 25/02* (2006.01)
*A01N 25/04* (2006.01)
(52) U.S. Cl.
CPC ............... *A01N 25/02* (2013.01); *A01N 25/04* (2013.01)

(58) Field of Classification Search
None
See application file for complete search history.

(56) References Cited

U.S. PATENT DOCUMENTS

| 5,206,255 | A | 4/1993 | Ubasawa et al. |
| 8,124,564 | B2 * | 2/2012 | Rochling et al. ............ 504/100 |
| 2005/0104844 | A1 | 5/2005 | Nakai et al. |
| 2011/0124505 | A1 | 5/2011 | Merlet et al. |

FOREIGN PATENT DOCUMENTS

| DE | 4341986 | 6/1995 |
| EP | 0453899 | 10/1991 |
| WO | 88/02216 | 4/1988 |
| WO | 95/15685 A1 | 6/1995 |
| WO | 2008/101629 | 8/2008 |
| WO | 2008/145063 | 12/2008 |
| WO | 2010/078852 | 7/2010 |

OTHER PUBLICATIONS

Baur et al., "Polydisperse Ethoxylated Fatty Alcohol Surfactants as Accelerators of Cuticular Penetration. 1. Effects of Ethoxy Chain Length and the Size of the Penetrants," Pestic. Sci. 1997,51: 131-152.
"Glossary of Common Names and Abbreviations of Herbicides," Weed Research, 1986, 26:441-445.
International Search Report for PCT/EP2012/065685 Mailed Oct. 24, 2012.

* cited by examiner

*Primary Examiner* — Kortney L Klinkel
*Assistant Examiner* — William Lee
(74) *Attorney, Agent, or Firm* — McBee Moore Woodward Vanik IP LLC

(57) ABSTRACT

The invention relates to the use of $C_{16}$-$C_{18}$-carboxylic acid dibutylamides in agrochemical formulations, agrochemical formulations which comprise such compounds and the use as tank mix additives.

18 Claims, No Drawings

USE AND AGROCHEMICAL COMPOSITION OF CARBOXYLIC ACID DIBUTYLAMIDES

CROSS REFERENCE TO RELATED APPLICATIONS

This application is a §371 National Stage Application of PCT/EP2012/065685, filed Aug. 10, 2012, which claims priority to European Application No. 11177196.0, filed Aug. 11, 2011, and U.S. Provisional Application No. 61/522,798, filed Aug. 12, 2011.

BACKGROUND OF THE INVENTION

1. Field of the Invention

The invention relates to the use of N,N-dibutylcarboxamides in agrochemical formulations and crop protection compositions, to agrochemical formulations and crop protection compositions comprising such compounds, and to use as a tankmix additive.

2. Description of Related Art

EP-A 0 453 899 discloses the use of N,N-dimethyl-$C_5$-$C_{19}$-alkylcarboxamides as crystallization inhibitors for particular azole fungicides having a tendency to crystallize, such as tebuconazole. The use of N,N-dibutylcarboxamides for this purpose or for improvement of the action of agrochemicals after deployment to the plant is neither disclosed nor suggested in this document.

US2005/104844 discloses that the N,N-dimethyl-$C_5$-$C_{19}$-alkylcarboxamides are penetrants for particular active ingredients, for example prothioconazoles. The use of N,N-dibutylcarboxamides for this purpose or for improvement of the action of agrochemicals after deployment to the plant is neither disclosed nor suggested in this document.

US2011/0124505 claims compositions comprising N,N-dimethyl-$C_5$-$C_{19}$-alkylcarboxamides as solvents for biocides and pesticides and various emulsifiers. The use of N,N-dibutylcarboxamides for this purpose or for improvement of the action of agrochemicals after deployment to the plant is neither disclosed nor suggested in this document.

In WO-A-1988/02216, DE-A-4341986 and WO-A-2008/145063, N,N-dialkylalkyl or- alkenylcarboxamides are used in agrochemical formulations for prevention of crystal formation in spray liquors. The teaching to use N,N-dialkylalkyl- or -alkenylcarboxamides as penetrants is not given in WO-A-1988/02216, DE-A-4341986 and WO-A-2008/145063.

WO-A-1988/02216 teaches the use of N,N-dialkylalkylcarboxamides for promotion of the penetration of medicaments through the human or animal skin. WO-A-1988/02216, however, does not disclose any agrochemical use, nor the use of the N,N-dibutyl-C16-C18-alkyl/alkenylcarboxamides used according to the invention.

WO-A-2010/078852 teaches agrochemical formulations in the form of suspoemulsions. WO-A-2010/078852, however, does not teach the use of the N,N-dibutyl-C16-C18-alkyl/alkenylcarboxamides used according to the invention in EC or OD formulations.

SUMMARY

It has now been found that, surprisingly, the N,N-dibutylcarboxamides used according to the invention are very much poorer solvents than the N,N-dimethylalkylcarboxamides. In spite of this, they are excellent and actually better additives for promoting the penetration of active agrochemical ingredients with very different physicochemical properties through the cuticle of the plant than the known N,N-dimethylcarboxamides (see examples 16 and 17). They are thus suitable for enhancing the biological efficacy of crop protection compositions. At the same time, they are several orders of magnitude less volatile from the leaf surface than the N,N-dimethylalkylcarboxamides.

In the case of the N,N-dibutylcarboxamides used in accordance with the invention, depending on the carboxylic acids or fatty acids of chain lengths C8-10, C12-14 (based on coconut fat) and C15-18 (based on tallow fat) present, some differences were discernible in the influence on the active ingredient penetration over the course of time. More particularly, it is found that the N,N-dibutyl-C16-C18-alkyl/alkenylcarboxamides in EC formulations lead to a distinct improvement in penetration over the N,N-dimethylcarboxamides (examples 16, 18 and 21).

In addition, it is found that the N,N-dibutyl-C16-C18-alkyl/alkenylcarboxamides have distinctly different penetration characteristics than the N,N-dibutyl-C12-C14-alkyl/alkenylcarboxamides and very particularly than the analogous N,N-dimethylcarboxamides. The N,N-dibutyl-C16-C18-alkyl/alkenylcarboxamides are absorbed into the leaf cuticle, but do not penetrate further into the leaf interior; as a result, they can ensure the penetration-enhancing effect over a long period. Especially the analogous N,N-dimethylcarboxamides have much higher penetration into the leaf, as a result of which the penetration-enhancing effect is restricted to the first few hours after spray application (example 22).

A further advantage of the N,N-dibutyl-C16-C18-alkyl/alkenylcarboxamides over the N,N-dibutyl-C8-C14-alkyl/alkenylcarboxamides is the substantial lack of volatility thereof.

The invention therefore provides for the use of carboxamides of the formula (I)

$$R^1\text{—CO—NR}^2R^3 \quad (I)$$

in which
R$^1$ is $C_{16}$-$C_{18}$-alkyl or $C_{16}$-$C_{18}$-alkenyl and
R$^2$ is $C_4$-alkyl and
R$^3$ is $C_4$-alkyl
for promoting the penetration of active agrochemical ingredients from the group of the fungicides or herbicides into plants.

DETAILED DESCRIPTION OF A PREFERRED EMBODIMENT

In this context, the penetration of the active agrochemical ingredient into plants means the penetration of the active agrochemical ingredient through the surface of the leaf into the plant.

R$^2$ and R$^3$ are preferably the same or different, more preferably identical alkyl groups having 4 carbon atoms, more preferably n-butyl, 1-methylpropyl or 2-methylpropyl, most preferably n-butyl.

R1 has 16-18 carbon atoms (tallow carboxylic acid dibutyl amide). In this context can be $C_{16}$-$C_{18}$-alkyl or $C_{16}$-$C_{18}$-alkenyl.

The N,N-dibutylcarboxamides are easy to prepare. A suitable preparation method is disclosed, for example, in WO-A-1995/015685 in example 1 on page 26 for N,N-di-n-propylhexanamide, which can also be applied analogously to the N,N-dibutylcarboxamides (e.g. example 16 on page 28 of WO-A-1995/015685).

Preference is given to using a mixture of at least two carboxamides of the formula (I). Preference is given to using a mixture based on the fatty acid composition of tallow. A typical raw material source is fatty acids from bovine tallow.

More preferably, the mixture used in accordance with the invention comprises both at least one carboxamide of the formula (I) in which R1 is $C_{16}$-$C_{18}$-alkyl and at least one carboxamide of the formula (I) in which R1 is $C_{16}$-$C_{18}$-alkenyl.

Particular preference is given to a mixture based on the fatty acid composition in bovine tallow. This comprises predominantly saturated and unsaturated fatty acids having an even number of carbon atoms. Fatty acids having an odd number of carbon atoms such as pentadecanoic acid (C15) or margaric acid (C17) are present only in small proportions.

Typically, bovine tallow contains more than 80% by weight, generally even more than 90% by weight, based on the sum of the weights of the fatty acids, of saturated and unsaturated C16-C18-fatty acids, especially palmitic acid (C16 saturated), palmitoleic acid (C16 partly unsaturated), margaric acid (C17 saturated), stearic acid (C18 saturated) and oleic acid (C18 partly unsaturated). Margaric acid and palmitoleic acid are present here only in relatively small amounts (of typically less than 10% by weight in total).

The N,N-dibutylcarboxamides have a volatility from the leaf surface reduced by several orders of magnitude compared to the N,N-dimethylcarboxamides used as solvents. The N,N-dibutylcarboxamides having an alkyl chain length R1 of $C_8$-$C_{10}$, however, still have a considerable volatility of practical relevance. Even shorter chain lengths are generally unsuitable because of their volatility for use as a biological efficacy-enhancing additive in agrochemical formulations. Even in the case of the N,N-dibutylcarboxamides having an alkyl chain length R1 of $C_{12}$-$C_{14}$, a certain volatility still exists. On the other hand, the N,N-dibutylcarboxamides having an alkyl chain length R1 of greater than $C_{18}$ i.e. $C_{20}$, $C_{22}$, or greater than $C_{22}$, are only of limited suitability because of their molecular size for significant penetration into the cuticle of plants and are thus ruled out as penetrants at the plant level. What are ideal are thus the N,N-dibutylcarboxamides having an alkyl chain length R1 of $C_{16}$-$C_{18}$.

The carboxamides of the formula (I) are used individually or in the form of mixtures. If carboxamides are mentioned in the description or the claims, what is meant is explicitly individual compounds or mixtures of several carboxamides.

The amount of one or more compounds of the formula (I) in the case of the inventive use in crop protection compositions can vary within wide limits according to the active ingredient and formulation type. The compounds of the formula (I) can be used in all standard agrochemical formulations, preferably in liquid formulations. The present invention also provides for the use of the carboxamides of the formula (I) for improving efficacy at the plant level as a tankmix additive, meaning that the carboxamides are added to a spray liquor produced from a concentrated formulation only directly before deployment. In principle, the compounds can also be introduced into solid formulations.

The inventive use of the carboxamides of the formula (I) is effected, for example, in formulations of active agrochemical ingredients and from ready-to-use crop protection compositions produced therefrom by dilution (preferably with water) (spray liquors).

The invention also relates to formulations in the form of emulsion concentrates (EC) or of dispersions in oil (OD) comprising at least one active agrochemical ingredient which is solid at room temperature (20° C.) and is from the group of the fungicides or herbicides and at least one carboxamide of the formula (I)

$$R^1—CO—NR^2R^3 \quad (I)$$

in which $R^1$ is $C_{16}$-$C_{18}$-alkyl or $C_{16}$-$C_{18}$-alkenyl and $R^2$ is $C_4$-alkyl and $R^3$ is $C_4$-alkyl, and at least one solvent and/or oil.

Preferably, the content of the at least one carboxamide of the formula (I) in the formulation is 1 to 50% by weight, more preferably 2 to 40% by weight, most preferably 5 to 25% by weight.

Because of their physical properties, such as state of matter, viscosity and melting point, N,N-dibutylcarboxamides are not very suitable for use in solid formulations such as granules (WG, WP). Suitable formulation types are liquid formulations. Because the carboxamides have some dissolution capacity, but it is not significant, use in suspoemulsions (SE), which comprise active ingredients in liquid and solid form, is not preferred.

Particular preference is given to use in emulsion concentrates (EC) in which the N,N-dibutylcarboxamides are distributed homogeneously in the homogeneous formulation and are applied to the leaf of the target crop in very intimate contact with the dissolved active ingredients by means of spray application. Particular preference is likewise given to use in dispersions in oil (OD) in which the N,N-dibutylcarboxamides are in direct contact with the active ingredient in the oil phase in the formulation and on the leaf after spray application.

The invention also relates to ready-to-use crop protection compositions comprising at least one active agrochemical ingredient which is solid at room temperature (20° C.) and is from the group of the fungicides or herbicides and at least one carboxamide of the formula (I)

$$R^1—CO—NR^2R^3 \quad (I)$$

in which $R^1$ is $C_{16}$-$C_{18}$-alkyl or $C_{16}$-$C_{18}$-alkenyl and $R^2$ is $C_4$-alkyl and $R^3$ is $C_4$-alkyl, and at least one solvent and/or oil and water.

Preferably, the content of the at least one carboxamide of the formula (I) in the crop protection composition is 0.01 to 10% by weight, more preferably 0.02 to 2% by weight, most preferably 0.05 to 0.2% by weight.

If a formulation/a crop protection composition comprises a plurality of carboxamides of the formula (I), the stated amount should be understood as the total content of all the carboxamides of the formula (I).

The radical definitions, value ranges and elucidations given above, in general terms or in areas of preference, can be combined with one another as desired, i.e. including combinations between the particular ranges and ranges of preference.

Suitable oils are especially vegetable oils or esters thereof or mineral oils or other organic solvents. Particularly suitable oils are sunflower oil, rapeseed oil or rapeseed oil methyl ester, and also paraffin oil or white oil, and aromatic hydrocarbon mixtures (preferably naphthalene-reduced), e.g. Solvesso™.

Suitable solvents in the context of this invention are especially also organic solvents such as N,N-dimethyldecanamide, N,N-dimethyloctanamide, N,N-dimethyldodedecanamide, gamma-butyrolactone, Rhodiasolv Polarclean™ (methyl 5-(dimethylamino)-2-methyl-5-oxopentanoate) N-methylpyrrolidone or aromatic hydrocarbon mixtures (preferably naphthalene-reduced), e.g. Solvesso™. Further suitable solvents are, for example, aromatic hydrocarbons, for example xylene, toluene or alkylnaphthalenes, chlorinated aromatic or aliphatic hydrocarbons, for example chlorobenzene, chloroethylene, or methylene chloride, aliphatic hydrocarbons, for example cyclohexane, alcohols, for example methanol, ethanol, isopropanol, butanol or glycol and the ethers and esters thereof (including fats and oils) and (poly)ethers, unsubstituted and substituted amines, amides, lactams (such as N-alkylpyrrolidones) and lactones, ketones, for example acetone, methyl ethyl ketone, methyl isobutyl ketone or cyclohexanone, strongly polar solvents such as dimethyl sulfoxide.

The active agrochemical ingredient used is more preferably prothioconazole. Particularly suitable formulations are those comprising
  15-35% by weight of prothioconazole and
  25-45% by weight of N,N-dimethyldecanamide and
  10-40% by weight of one or more emulsifiers, preferably castor oil polyglycol ether esters or a mixture of ethoxypropoxytristyrylphenol (block copolymer) and tristyrylphenol ethoxylate having an average of 16 EO units or a mixture of 2-ethylhexanol propylene ethylene glycol ether, ethoxypropoxytristyrylphenol (block copolymer), alkoxylated ethylenediamine having an average of 16 EO and 16 PO units and tristyrylphenol ethoxylate having an average of 16 EO units or a mixture of the emulsifiers mentioned in another combination and
  0.01-1.0% by weight of defoamer, preferably silicone antifoam emulsion, and
  5-30% by weight of N,N-dibutyl-C16-C18-alkylcarboxamide and N,N-dibutyl-C16-C18-alkenylcarboxamide (in total).

The mechanism of action of the carboxamides as penetrants is essentially independent of the type of active agrochemical ingredient used. Therefore, the use thereof in formulations and crop protection compositions comprising at least one active ingredient from the group of the fungicides or herbicides, the biological efficacy of which can be increased by increased penetration into a crop plant or weed plant, is an option.

Examples of fungicides include:

(1) Ergosterol biosynthesis inhibitors, for example aldimorph, azaconazole, bitertanol, bromuconazole, cyproconazole, diclobutrazole, difenoconazole, diniconazole, diniconazole-M, dodemorph, dodemorph acetate, epoxiconazole, etaconazole, fenarimol, fenbuconazole, fenhexamid, fenpropidin, fenpropimorph, fluquinconazole, flurprimidol, flusilazole, flutriafol, furconazole, furconazole-cis, hexaconazole, imazalil, imazalil sulfate, imibenconazole, ipconazole, metconazole, myclobutanil, naftifin, nuarimol, oxpoconazole, paclobutrazole, pefurazoate, penconazole, piperalin, prochloraz, propiconazole, prothioconazole, pyributicarb, pyrifenox, quinconazole, simeconazole, spiroxamine, tebuconazole, terbinafine, tetraconazole, triadimefon, triadimenol, tridemorph, triflumizole, triforine, triticonazole, uniconazole, uniconazole-p, viniconazole, voriconazole, 1-(4-chlorophenyl)-2-(1H-1,2,4-triazol-1-yl)cycloheptanol, methyl 1-(2,2-dimethyl-2,3-dihydro-1H-inden-1-yl)-1H-imidazole-5-carboxylate, N'-{5-(difluoromethyl)-2-methyl-4-[3-(trimethylsilyl)propoxy]phenyl}-N-ethyl-N-methylimidoformamide, N-ethyl-N-methyl-N'-{2-methyl-5-(trifluoromethyl)-4-[3-(trimethylsilyl)propoxy]phenyl}imidoformamide and O-[1-(4-methoxyphenoxy)-3,3-dimethylbutan-2-yl]1H-imidazole-1-carbothioate.

(2) Respiration inhibitors (respiratory chain inhibitors), for example bixafen, boscalid, carboxin, diflumetorim, fenfuram, fluopyram, flutolanil, fluxapyroxad, furametpyr, furmecyclox, isopyrazam mixture of the syn-epimeric racemate 1RS,4SR,9RS and of the anti-epimeric racemate 1RS,4SR,9SR, isopyrazam (anti-epimeric racemate), isopyrazam (anti-epimeric enantiomer 1R,4S,9S), isopyrazam (anti-epimeric enantiomer 1S,4R,9R), isopyrazam (syn-epimeric racemate 1RS,4SR,9RS), isopyrazam (syn-epimeric enantiomer 1R,4S,9R), isopyrazam (syn-epimeric enantiomer 1S,4R,9S), mepronil, oxycarboxin, penflufen, penthiopyrad, sedaxane, thifluzamid, 1-methyl-N-[2-(1,1,2,2-tetrafluoroethoxy)phenyl]-3-(trifluoromethyl)-1H-pyrazole-4-carboxamide, 3-(difluoromethyl)-1-methyl-N-[2-(1,1,2,2-tetrafluoroethoxy)phenyl]-1H-pyrazole-4-carboxamide, 3-(difluoromethyl)-N-[4-fluoro-2-(1,1,2,3,3,3-hexafluoropropoxy)phenyl]-1-methyl-1H-pyrazole-4-carboxamide, N-[1-(2,4-dichlorophenyl)-1-methoxypropan-2-yl]-3-(difluoromethyl)-1-methyl-1H-pyrazole-4-carboxamide, 5,8-difluoro-N-[2-(2-fluoro-4-{[4-(trifluoromethyl)pyridin-2-yl]oxy}phenyl)ethyl]quinazoline-4-amine, N-[9-(dichloromethylene)-1,2,3,4-tetrahydro-1,4-methanonaphthalen-5-yl]-3-(difluoromethyl)-1-methyl-1H-pyrazole-4-carboxamide, N-[(1S,4R)-9-(dichloromethylene)-1,2,3,4-tetrahydro-1,4-methanonaphthalen-5-yl]-3-(difluoromethyl)-1-methyl-1H-pyrazole-4-carboxamide and N-[(1R,4S)-9-(dichloromethylene)-1,2,3,4-tetrahydro-1,4-methanonaphthalen-5-yl]-3-(difluoromethyl)-1-methyl-1H-pyrazole-4-carboxamide.

(3) Respiration inhibitors (respiratory chain inhibitors) acting on complex III of the respiratory chain, for example ametoctradin, amisulbrom, azoxystrobin, cyazofamid, coumethoxystrobin, coumoxystrobin, dimoxystrobin, enestroburin, famoxadone, fenamidone, fenoxystrobin, fluoxastrobin, kresoxim-methyl, metominostrobin, orysastrobin, picoxystrobin, pyraclostrobin, pyrametostrobin, pyraoxystrobin, pyribencarb, triclopyricarb, trifloxystrobin, (2E)-2-(2-{[6-(3-chloro-2-methylphenoxy)-5-fluoropyrimidin-4-yl]oxy}phenyl)-2-(methoxyimino)-N-methylethanamide, (2E)-2-(methoxyimino)-N-methyl-2-(2-{[({(1E)-1-[3-(trifluoromethyl)phenyl]ethylidene}amino)oxy]methyl}phenyl)ethanamide, (2E)-2-(methoxyimino)-N-methyl-2-{2-[(E)-({1-[3-(trifluoromethyl)phenyl]ethoxy}imino)methyl]phenyl}ethanamide, (2E)-2-{2-[({[(1E)-1-(3-{[(E)-1-fluoro-2-phenylethenyl]oxy}phenyl)ethylidene]amino}oxy)methyl]phenyl}-2-(methoxyimino)-N-methylethanamide, (2E)-2-{2-[({[(2E,3E)-4-(2,6-dichlorophenyl)but-3-en-2-ylidene]amino}oxy)methyl]phenyl}-2-(methoxyimino)-N-methylethanamide, 2-chloro-N-(1,1,3-trimethyl-2,3-dihydro-1H-inden-4-yl)pyridine-3-carboxamide, 5-methoxy-2-methyl-4-(2-{[({(1E)-1-[3-(trifluoromethyl)phenyl]ethylidene}amino)oxy]methyl}phenyl)-2,4-dihydro-3H-1,2,4-triazol-3-one, methyl (2E)-2-{2-[({cyclopropyl[(4-methoxyphenyl)imino]methyl}sulfanyl)methyl]phenyl}-3-methoxyprop-2-enoate, N-(3-ethyl-3,5,5-trimethylcyclohexyl)-3-(formylamino)-2-hydroxybenzamide, 2-{2-[(2,5-dimethylphenoxy)methyl]

phenyl}-2-methoxy-N-methylacetamide and (2R)-2-{2-[(2,5-dimethylphenoxy)methyl]phenyl}-2-methoxy-N-methylacetamide.

(4) Mitosis and cell division inhibitors, for example benomyl, carbendazim, chlorfenazole, diethofencarb, ethaboxam, fluopicolide, fuberidazole, pencycuron, thiabendazole, thiophanate-methyl, thiophanate, zoxamide, 5-chloro-7-(4-methylpiperidin-1-yl)-6-(2,4,6-trifluorophenyl) [1,2,4]triazolo[1,5-a]pyrimidine and 3-chloro-5-(6-chloropyridin-3-yl)-6-methyl-4-(2,4,6-trifluorophenyl)pyridazine.

(5) Compounds with multisite activity, for example Bordeaux mixture, captafol, captan, chlorothalonil, copper preparations such as copper hydroxide, copper naphthenate, copper oxide, copper oxychloride, copper sulfate, dichlofluanid, dithianon, dodine, dodine free base, ferbam, fluorofolpet, folpet, guazatine, guazatine acetate, iminoctadine, iminoctadine albesilate, iminoctadine triacetate, mancopper, mancozeb, maneb, metiram, metiram zinc, oxine-copper, propamidine, propineb, sulfur and sulfur preparations, for example calcium polysulfide, thiram, tolylfluanid, zineb and ziram.

(6) Resistance inductors, for example acibenzolar-S-methyl, isotianil, probenazole and tiadinil.

(7) Amino acid and protein biosynthesis inhibitors, for example andoprim, blasticidin-S, cyprodinil, kasugamycin, kasugamycin hydrochloride hydrate, mepanipyrim, pyrimethanil and 3-(5-fluoro-3,3,4,4-tetramethyl-3,4-dihydroisoquinolin-1-yl)quinoline.

(8) ATP production inhibitors, for example fentin acetate, fentin chloride, fentin hydroxide and silthiofam.

(9) Cell wall synthesis inhibitors, for example benthiavalicarb, dimethomorph, flumorph, iprovalicarb, mandipropamid, polyoxins, polyoxorim, validamycin A and valifenalate.

(10) Lipid and membrane synthesis inhibitors, for example biphenyl, chloroneb, dicloran, edifenphos, etridiazole, iodocarb, iprobenfos, isoprothiolane, propamocarb, propamocarb hydrochloride, prothiocarb, pyrazophos, quintozene, tecnazene and tolclofos-methyl.

(11) Melanin biosynthesis inhibitors, for example carpropamid, diclocymet, fenoxanil, fthalide, pyroquilon, tricyclazole and 2,2,2-trifluoroethyl {3-methyl-1-[(4-methylbenzoyl)amino]butan-2-yl}carbamate.

(12) Nucleic acid synthesis inhibitors, for example benalaxyl, benalaxyl-M (kiralaxyl), bupirimate, clozylacon, dimethirimol, ethirimol, furalaxyl, hymexazol, metalaxyl, metalaxyl-M (mefenoxam), ofurace, oxadixyl and oxolinic acid.

(13) Signal transduction inhibitors, for example chlozolinate, fenpiclonil, fludioxonil, iprodione, procymidone, quinoxyfen and vinclozolin.

(14) Decouplers, for example binapacryl, dinocap, ferimzone, fluazinam and meptyldinocap.

(15) Further compounds, for example benthiazole, bethoxazin, capsimycin, carvone, chinomethionat, pyriofenone (chlazafenone), cufraneb, cyflufenamid, cymoxanil, cyprosulfamide, dazomet, debacarb, dichlorophen, diclomezine, difenzoquat, difenzoquat methylsulfate, diphenylamine, ecomat, fenpyrazamine, flumetover, fluoromide, flusulfamide, flutianil, fosetyl-aluminium, fosetyl-calcium, fosetyl-sodium, hexachlorobenzene, irumamycin, methasulfocarb, methyl isothiocyanate, metrafenon, mildiomycin, natamycin, nickel dimethyldithiocarbamate, nitrothal-isopropyl, octhilinone, oxamocarb, oxyfenthiin, pentachlorophenol and salts thereof, phenothrin, phosphoric acid and salts thereof, propamocarb-fosetylate, propanosine-sodium, proquinazid, pyrimorph, (2E)-3-(4-tert-butylphenyl)-3-(2-chloropyridin-4-yl)-1-(morpholin-4-yl)prop-2-en-1-one, (2Z)-3-(4-tert-butylphenyl)-3-(2-chloropyridin-4-yl)-1-(morpholin-4-yl)prop-2-en-1-one, pyrrolnitrin, tebufloquin, tecloftalam, tolnifanid, triazoxide, trichlamide, zarilamide, (3S,6S,7R,8R)-8-benzyl-3-[({3-[(isobutyryloxy)methoxy]-4-methoxypyridin-2-yl}carbonyl)amino]-6-methyl-4,9-dioxo-1,5-dioxonan-7-yl 2-methylpropanoate, 1-(4-{4-[(5R)-5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone, 1-(4-{4-[(5S)-5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone, 1-(4-{4-[5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone, 1-(4-methoxyphenoxy)-3,3-dimethylbutan-2-yl 1H-imidazole-1-carboxylate, 2,3,5,6-tetrachloro-4-(methylsulfonyl)pyridine, 2,3-dibutyl-6-chlorothieno[2,3-d]pyrimidin-4(3H)-one, 2,6-dimethyl-1H,5H-[1,4]dithiino[2,3-c:5,6-c]dipyrrole-1,3,5,7(2H,6H)-tetrone, 2-[5-methyl-3-(trifluoromethyl)-1H-pyrazol-1-yl]-1-(4-{4-[(5R)-5-phenyl-4,5-dihydro-1,2-oxazol-3-yl]-1,3-thiazol-2-yl}piperidin-1-yl)ethanone, 2-[5-methyl-3-(trifluoromethyl)-1H-pyrazol-1-yl]-1-(4-{4-[(5S)-5-phenyl-4,5-dihydro-1,2-oxazol-3-yl]-1,3-thiazol-2-yl}piperidin-1-yl)ethanone, 2-[5-methyl-3-(trifluoromethyl)-1H-pyrazol-1-yl]-1-{4-[4-(5-phenyl-4,5-dihydro-1,2-oxazol-3-yl)-1,3-thiazol-2-yl]piperidin-1-yl}ethanone, 2-butoxy-6-iodo-3-propyl-4H-chromen-4-one, 2-chloro-5-[2-chloro-1-(2,6-difluoro-4-methoxyphenyl)-4-methyl-1H-imidazol-5-yl]pyridine, 2-phenylphenol and salts thereof, 3-(4,4,5-trifluoro-3,3-dimethyl-3,4-dihydroisoquinolin-1-yl)quinoline, 3,4,5-trichloropyridine-2,6-dicarbonitrile, 3-[5-(4-chlorophenyl)-2,3-dimethyl-1,2-oxazolidin-3-yl]pyridine, 3-chloro-5-(4-chlorophenyl)-4-(2,6-difluorophenyl)-6-methylpyridazine, 4-(4-chlorophenyl)-5-(2,6-difluorophenyl)-3,6-dimethylpyridazine, 5-amino-1,3,4-thiadiazole-2-thiol, 5-chloro-N'-phenyl-N'-(prop-2-yn-1-yl)thiophene-2-sulfonohydrazide, 5-fluoro-2-[(4-fluorobenzyl)oxy]pyrimidine-4-amine, 5-fluoro-2-[(4-methylbenzyl)oxy]pyrimidine-4-amine, 5-methyl-6-octyl[1,2,4]triazolo[1,5-a]pyrimidine-7-amine, ethyl (2Z)-3-amino-2-cyano-3-phenylprop-2-enoate, N'-(4-{[3-(4-chlorobenzyl)-1,2,4-thiadiazol-5-yl]oxy}-2,5-dimethylphenyl)-N-ethyl-N-methylimidoformamide, N-(4-chlorobenzyl)-3-[3-methoxy-4-(prop-2-yn-1-yloxy)phenyl]propanamide, N-[(4-chlorophenyl)(cyano)methyl]-3-[3-methoxy-4-(prop-2-yn-1-yloxy)phenyl]propanamide, N-[(5-bromo-3-chloropyridin-2-yl)methyl]-2,4-dichloropyridine-3-carboxamide, N-[1-(5-bromo-3-chloropyridin-2-yl)ethyl]-2,4-dichloropyridine-3-carboxamide, N-[1-(5-bromo-3-chloropyridin-2-yl)ethyl]-2-fluoro-4-iodopyridine-3-carboxamide, N-{(E)-[(cyclopropylmethoxy)imino][6-(difluoromethoxy)-2,3-difluorophenyl]methyl}-2-phenylacetamide, N-{(Z)-[(cyclopropylmethoxy)imino][6-(difluoromethoxy)-2,3-difluorophenyl]methyl}-2-phenylacetamide, N'-{4-[(3-tert-butyl-4-cyano-1,2-thiazol-5-yl)oxy]-2-chloro-5-methylphenyl}-N-ethyl-N-methylimidoformamide, N-methyl-2-(1-{[5-methyl-3-(trifluoromethyl)-1H-pyrazol-1-yl]acetyl}piperidin-4-yl)-N-(1,2,3,4-tetrahydronaphthalen-1-yl)-1,3-thiazole-4-carboxamide, N-methyl-2-(1-{[5-methyl-3-(trifluoromethyl)-1H-pyrazol-1-yl]acetyl}piperidin-4-yl)-N-[(1R)-1,2,3,4-tetrahydronaphthalen-1-yl]-1,3-thiazole-4-carboxamide, N-methyl-2-(1-{[5-methyl-3-(trifluoromethyl)-1H-pyrazol-1-yl]acetyl}piperidin-4-yl)-N-[(1S)-1,2,3,4-tetrahydronaphthalen-1-yl]-1,3-thiazole-4-carboxamide, pentyl {6-[({[(1-methyl-1H-tetrazol-5-yl)(phenyl)methylidene]amino}oxy)methyl]pyridin-2-yl}carbamate, phenazine-1-carboxylic acid, quinolin-8-ol, quinolin-8-ol sulfate (2:1) and tert-butyl {6-[({[(1-methyl-1H-tetrazol-5-yl)(phenyl)methylene]amino}oxy)methyl]pyridin-2-yl}carbamate.

(16) Further compounds, for example 1-methyl-3-(trifluoromethyl)-N-[2'-(trifluoromethyl)biphenyl-2-yl]-1H-pyrazole-4-carboxamide, N-(4'-chlorobiphenyl-2-yl)-3-(difluoromethyl)-1-methyl-1H-pyrazole-4-carboxamide, N-(2',4'-dichlorobiphenyl-2-yl)-3-(difluoromethyl)-1-methyl-1H-pyrazole-4-carboxamide, 3-(difluoromethyl)-1-methyl-N-[4'-(trifluoromethyl)biphenyl-2-yl]-1H-pyrazole-4-carboxamide, N-(2',5'-difluorobiphenyl-2-yl)-1-methyl-3-(trifluoromethyl)-1H-pyrazole-4-carboxamide, 3-(difluoromethyl)-1-methyl-N-[4'-(prop-1-yn-1-yl)biphenyl-2-yl]-1H-pyrazole-4-carboxamide, 5-fluoro-1,3-dimethyl-N-[4'-(prop-1-yn-1-yl)biphenyl-2-yl]-1H-pyrazole-4-carboxamide, 2-chloro-N-[4'-(prop-1-yn-1-yl)biphenyl-2-yl]pyridine-3-carboxamide, 3-(difluoromethyl)-N-[4'-(3,3-dimethylbut-1-yn-1-yl)biphenyl-2-yl]-1-methyl-1H-pyrazole-4-carboxamide, N-[4'-(3,3-dimethylbut-1-yn-1-yl)biphenyl-2-yl]-5-fluoro-1,3-dimethyl-1H-pyrazole-4-carboxamide, 3-(difluoromethyl)-N-(4'-ethynylbiphenyl-2-yl)-1-methyl-1H-pyrazole-4-carboxamide, N-(4'-ethynylbiphenyl-2-yl)-5-fluoro-1,3-dimethyl-1H-pyrazole-4-carboxamide, 2-chloro-N-(4'-ethynylbiphenyl-2-yl)pyridine-3-carboxamide, 2-chloro-N-[4'-(3,3-dimethylbut-1-yn-1-yl)biphenyl-2-yl]pyridine-3-carboxamide, 4-(difluoromethyl)-2-methyl-N-[4'-(trifluoromethyl)biphenyl-2-yl]-1,3-thiazole-5-carboxamide, 5-fluoro-N-[4'-(3-hydroxy-3-methylbut-1-yn-1-yl)biphenyl-2-yl]-1,3-dimethyl-1H-pyrazole-4-carboxamide, 2-chloro-N-[4'-(3-hydroxy-3-methylbut-1-yn-1-yl)biphenyl-2-yl]pyridine-3-carboxamide, 3-(difluoromethyl)-N-[4'-(3-methoxy-3-methylbut-1-yn-1-yl)biphenyl-2-yl]-1-methyl-1H-pyrazole-4-carboxamide, 5-fluoro-N-[4'-(3-methoxy-3-methylbut-1-yn-1-yl)biphenyl-2-yl]-1,3-dimethyl-1H-pyrazole-4-carboxamide, 2-chloro-N-[4'-(3-methoxy-3-methylbut-1-yn-1-yl)biphenyl-2-yl]pyridine-3-carboxamide, (5-bromo-2-methoxy-4-methylpyridin-3-yl)(2,3,4-trimethoxy-6-methylphenyl)methanone, N-[2-(4-{[3-(4-chlorophenyl)prop-2-yn-1-yl]oxy}-3-methoxyphenyl)ethyl]-N2-(methylsulfonyl)valinamide, 4-oxo-4-[(2-phenylethyl)amino]butanoic acid and but-3-yn-1-yl {6-[({[(Z)-(1-methyl-1H-tetrazol-5-yl)(phenyl)methylene]amino}oxy)methyl]pyridin-2-yl}carbamate.

All mixing components mentioned in classes (1) to (16) can, if they are capable on the basis of their functional groups, optionally form salts with suitable bases or acids.

Examples of herbicides include:

Usable combination partners for the inventive compounds in mixture formulations or in a tankmix are, for example, known active ingredients based on inhibition of, for example, acetolactate synthase, acetyl-CoA carboxylase, cellulose synthase, enolpyruvylshikimate-3-phosphate synthase, glutamine synthetase, p-hydroxyphenylpyruvate dioxygenase, phytoendesaturase, photosystem I, photosystem II, protoporphyrinogen oxidase, as described, for example, in Weed Research 26 (1986) 441-445 or "The Pesticide Manual", 15th edition, The British Crop Protection Council and the Royal Soc. of Chemistry, 2006 and literature cited therein. Examples of known herbicides or plant growth regulators which can be combined with the inventive compounds include the active ingredients which follow (the compounds are designated by the "common name" according to the International Organization for Standardization (ISO) or by the chemical name or by the code number) and always encompass all use forms, such as acids, salts, esters and isomers, such as stereoisomers and optical isomers. One administration form or else, in some cases, more than one administration form is mentioned:

acetochlor, acibenzolar, acibenzolar-S-methyl, acifluorfen, acifluorfen-sodium, aclonifen, alachlor, allidochlor, alloxydim, alloxydim-sodium, ametryne, amicarbazone, amidochlor, amidosulfuron, aminocyclopyrachlor, aminocyclopyrachlor-potassium, aminocyclopyrachlor-methyl, aminopyralid, amitrole, ammonium sulfamate, ancymidol, anilofos, asulam, atrazine, aviglycine, azafenidin, azimsulfuron, aziprotryne, beflubutamid, benazolin, benazolin-ethyl, bencarbazone, benfluralin, benfuresate, bensulide, bensulfuron, bensulfuron-methyl, bentazone, benzfendizone, benzobicyclon, benzofenap, benzofluor, benzoylprop, benzyladenine, bicyclopyrone, bifenox, bilanafos, bilanafos-sodium, bispyribac, bispyribac-sodium, bromacil, bromobutide, bromofenoxim, bromoxynil, bromuron, buminafos, busoxinone, butachlor, butafenacil, butamifos, butenachlor, butralin, butroxydim, butylate, cafenstrole, carbaryl, carbetamide, carfentrazone, carfentrazone-ethyl, carvone, chlorocholine chloride, chlomethoxyfen, chloramben, chlorazifop, chlorazifop-butyl, chlorbromuron, chlorbufam, chlorfenac, chlorfenac-sodium, chlorfenprop, chlorflurenol, chlorflurenol-methyl, chloridazon, chlorimuron, chlorimuron-ethyl, chlormequat-chloride, chlornitrofen, 4-chlorophenoxyacetic acid, chlorophthalim, chlorpropham, chlorthal-dimethyl, chlortoluron, chlorsulfuron, cinidon, cinidon-ethyl, cinmethylin, cinosulfuron, clethodim, clodinafop, clodinafop-propargyl, clofencet, clomazone, clomeprop, cloprop, clopyralid, cloransulam, cloransulam-methyl, cloxyfonac, cumyluron, cyanamide, cyanazine, cyclanilide, cycloate, cyclosulfamuron, cycloxydim, cycluron, cyhalofop, cyhalofop-butyl, cyperquat, cyprazine, cyprazole, cytokinine, 2,4-D, 2,4-DB, daimuron/dymron, dalapon, daminozide, dazomet, n-decanol, desmedipham, desmetryn, detosyl-pyrazolate (DTP), diallate, diaminozide, dicamba, dichlobenil, dichlorprop, dichlorprop-P, diclofop, diclofop-methyl, diclofop-P-methyl, diclosulam, diethatyl, diethatyl-ethyl, difenoxuron, difenzoquat, diflufenican, diflufenzopyr, diflufenzopyr-sodium, dikegulac-sodium, dimefuron, dimepiperate, dimethachlor, dimethametryn, dimethenamid, dimethenamid-P, dimethipin, dimetrasulfuron, dinitramine, dinoseb, dinoterb, diphenamid, diisopropylnaphthalene, dipropetryn, diquat, diquat-dibromide, dithiopyr, diuron, DNOC, eglinazine-ethyl, endothal, EPTC, esprocarb, ethalfluralin, ethametsulfuron, ethametsulfuron-methyl, ethyl naphthylacetate, ethephon, ethidimuron, ethiozin, ethofumesate, ethoxyfen, ethoxyfen-ethyl, ethoxysulfuron, etobenzanid, F-5331, i.e. N-[2-chloro-4-fluoro-5-[4-(3-fluoropropyl)-4,5-dihydro-5-oxo-1H-tetrazol-1-yl]phenyl]ethanesulfonamide, F-7967, i.e. 3-[7-chloro-5-fluoro-2-(trifluoromethyl)-1H-benzimidazol-4-yl]-1-methyl-6-(trifluoromethyl)pyrimidine-2,4(1H,3H)-dione, fenoprop, fenoxaprop, fenoxaprop-P, fenoxaprop-ethyl, fenoxaprop-P-ethyl, fenoxasulfone, fentrazamide, fenuron, flamprop, flamprop-M-isopropyl, flamprop-M-methyl, flazasulfuron, florasulam, fluazifop, fluazifop-P, fluazifop-butyl, fluazifop-P-butyl, fluazolate, flucarbazone, flucarbazone-sodium, flucetosulfuron, fluchloralin, flufenacet (thiafluamide), flufenpyr, flufenpyr-ethyl, flumetralin, flumetsulam, flumiclorac, flumiclorac-pentyl, flumioxazin, flumipropyn, fluometuron, fluorodifen, fluoroglycofen, fluoroglycofen-ethyl, flupoxam, flupropacil, flupropanate, flupyrsulfuron, flupyrsulfuron-methyl-sodium, flurenol, flurenol-butyl, fluridone, fluorochloridone, fluroxypyr, fluroxypyr-meptyl, flurprimidol, flurtamone, fluthiacet, fluthiacet-methyl, fluthiamide, fomesafen, foramsulfuron, forchlorfenuron, fosamine, furyloxyfen, gibberellic acid, glufosinate, glufosinate-ammonium, glufosinate-P, glufosinate-P-ammonium, glufosinate-P-sodium, glyphosate, glyphosate-isopropylammonium, H-9201, i.e. 0-(2,4-dimethyl-6-nitrophenyl) O-ethyl isopropylphosphoramidothioate, halosafen, halosulfuron, halosulfuron-methyl, haloxyfop, haloxyfop-P, haloxyfop-ethoxyethyl, haloxyfop-P-ethoxyethyl, haloxyfop-methyl, haloxyfop-P-methyl, hexazinone, HW-02, i.e. 1-(dimethoxyphosphoryl)ethyl (2,4-dichlorophenoxy)acetate, imazamethabenz, imazamethabenz-methyl, imazamox, imazamox-ammonium, imazapic, imazapyr, imazapyr-isopropylammonium, imazaquin, imazaquin-ammonium, imazethapyr, imazethapyr-ammonium, imazosulfuron, inabenfide, indanofan, indaziflam, indoleacetic acid (IAA), 4-indol-3-ylbutyric acid (IBA), iodosulfuron, iodosulfuron-methyl-sodium, iofensulfuron, iofensulfuron-sodium, ioxynil, ipfencarbazone, isocarbamid, isopropalin, isoproturon, isouron, isoxaben, isoxachlortole, isoxaflutole, isoxapyrifop, KUH-043, i.e. 3-({[5-(difluoromethyl)-1-methyl-3-(trifluoromethyl)-1H-pyrazol-4-yl]methyl}sulfonyl)-5,5-dimethyl-4,5-dihydro-1,2-oxazole, karbutilate, ketospiradox, lactofen, lenacil, linuron, maleic hydrazide, MCPA, MCPB, MCPB-methyl, -ethyl and -sodium, mecoprop, mecoprop-sodium, mecoprop-butotyl, mecoprop-P-butotyl, mecoprop-P-dimethylammonium, mecoprop-P-2-ethylhexyl, mecoprop-P-potassium, mefenacet, mefluidide, mepiquat-chloride, mesosulfuron, mesosulfuron-methyl, mesotrione, methabenzthiazuron, metam, metamifop, metamitron, metazachlor, metazasulfuron, methazole, methiopyrsulfuron, methiozolin, methoxyphenone, methyldymron, 1-methylcyclopropene, methyl isothiocyanate, metobenzuron, metobromuron, metolachlor, S-metolachlor, metosulam, metoxuron, metribuzin, metsulfuron, metsulfuron-methyl, molinate, monalide, monocarbamide, monocarbamide dihydrogensulfate, monolinuron, monosulfuron, monosulfuron ester, monuron, MT-128, i.e. 6-chloro-N-[(2E)-3-chloroprop-2-en-1-yl]-5-methyl-N-phenylpyridazine-3-amine, MT-5950, i.e. N-[3-chloro-4-(1-methylethyl)phenyl]-2-methylpentanamide, NGGC-011, 1-naphthylacetic acid (NAA), naphthylacetamide (NAAm), 2-naphthoxyacetic acid, naproanilide, napropamide, naptalam, NC-310, i.e. 4-(2,4-dichlorobenzoyl)-1-methyl-5-benzyloxypyrazole, neburon, nicosulfuron, nipyraclofen, nitralin, nitrofen, nitroguaiacolate, nitrophenolate-sodium (isomer mixture), nitrofluorfen, nonanoic acid, norflurazon, orbencarb, orthosulfamuron, oryzalin, oxadiargyl, oxadiazon, oxasulfuron, oxaziclomefone, oxyfluorfen, paclobutrazole, paraquat, paraquat dichloride, pelargonic acid (nonanoic acid), pendimethalin, pendralin, penoxsulam, pentanochlor, pentoxazone, perfluidone, pethoxamid, phenisopham, phenmedipham, phenmedipham-ethyl, picloram, picolinafen, pinoxaden, piperophos, pirifenop, pirifenop-butyl, pretilachlor, primisulfuron, primisulfuron-methyl, probenazole, profluazole, procyazine, prodiamine, prifluraline, profoxydim, prohexadione, prohexadione-calcium, prohydrojasmone, prometon, prometryn, propachlor, propanil, propaquizafop, propazine, propham, propisochlor, propoxycarbazone, propoxycarbazone-sodium, propyrisulfuron, propyzamide, prosulfalin, prosulfocarb, prosulfuron, prynachlor, pyraclonil, pyraflufen, pyraflufen-ethyl, pyrasulfotole, pyrazolynate (pyrazolate), pyrazosulfuron, pyrazosulfuron-ethyl, pyrazoxyfen, pyribambenz, pyribambenz-isopropyl, pyribambenz-propyl, pyribenzoxim, pyributicarb, pyridafol, pyridate, pyriftalid, pyriminobac, pyriminobac-methyl, pyrimisulfan, pyrithiobac, pyrithiobac-sodium, pyroxasulfone, pyroxsulam, quinclorac, quinmerac, quinoclamine, quizalofop, quizalofop-ethyl, quizalofop-P, quizalofop-P-ethyl, quizalofop-P-tefuryl, rimsulfuron, saflufenacil, secbumeton, sethoxydim, siduron, simazine, simetryn, SN-106279, i.e. methyl (2R)-2-({7-[2-chloro-4-(trifluoromethyl)phenoxy]-2-naphthyl}oxy)propanoate, sulcotrione, sulfallate (CDEC), sulfentrazone, sulfometuron, sulfometuron-methyl, sulfosate (glyphosate-trimesium), sulfosulfuron, SW-065, SYN-523, SYP-249, i.e. 1-ethoxy-3-methyl-1-oxobut-3-en-2-yl 5-[2-chloro-4-(trifluoromethyl)phenoxy]-2-nitrobenzoate, SYP-300, i.e. 1-[7-fluoro-3-oxo-4-(prop-2-yn-1-yl)-3,4-dihydro-2H-1,4-benzoxazin-6-yl]-3-propyl-2-thioxoimidazolidine-4,5-dione, tebutam, tebuthiuron, tecnazene, tefuryltrione, tembotrione, tepraloxydim, terbacil, terbucarb, terbuchlor, terbumeton, terbuthylazine, terbutryne, thenylchlor, thiafluamide, thiazafluron, thiazopyr, thidiazimin, thidiazuron, thiencarbazone, thiencarbazone-methyl, thifensulfuron, thifensulfuron-methyl, thiobencarb, tiocarbazil, topramezone, tralkoxydim, triafamone, triallate, triasulfuron, triaziflam, triazofenamide, tribenuron, tribenuron-methyl, tribufos, trichloroacetic acid (TCA), triclopyr, tridiphane, trietazine, trifloxysulfuron, trifloxysulfuron-sodium, trifluralin, triflusulfuron, triflusulfuron-methyl, trimeturon, trinexapac, trinexapac-ethyl, tritosulfuron, tsitodef, uniconazole, uniconazole-P, vernolate, ZJ-0862, i.e. 3,4-dichloro-N-{2-[(4,6-dimethoxypyrimidin-2-yl)oxy]benzyl}aniline, and the following compounds:

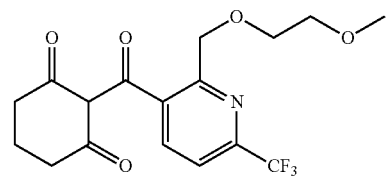

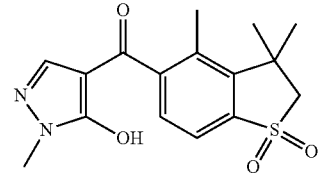

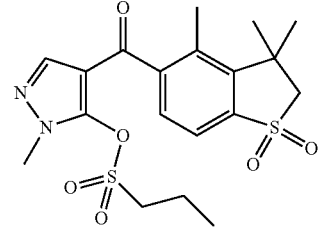

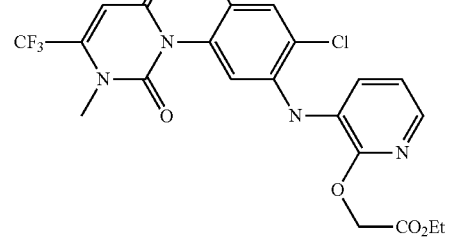

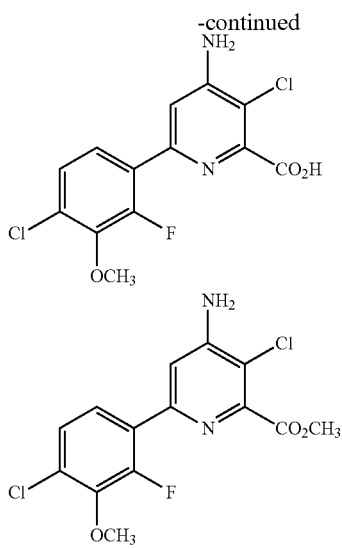

Preferred active agrochemical ingredients are triazoles and strobilurins, especially cyproconazole, epoxiconazole, metconazole, propiconazole, prothioconazole, tebuconazole, and also azoxystrobin, fluoxastrobin, kresoxim-methyl, metominostrobin, picoxystrobin, pyraclostrobin and trifloxystrobin. Likewise preferred are isopyrazam, indaziflam, fluopyram, fluxapyroxad and bixafen. Likewise preferred are all systemic leaf-applied or post-emergence herbicides and safeners, especially amidosulfuron, bromoxynil, cyprosulfamide, 2,4-D, glufosinate, glyphosate, iodosulfuron-methyl, isoxadifen-ethyl, mefenpyr, mesosulfuron, mesotrione, metamitron, phenmedipham, sulcotrione, tembotrione and thiencarbazone-methyl.

The present invention further relates to formulations and use forms prepared therefrom as crop protection compositions and/or pesticides, for example drench, drip and spray liquors, comprising at least one of the inventive N,N-dibutylcarboxamides. The use forms optionally comprise further crop protection agents and/or pesticides and/or action-improving adjuvants, such as penetrants, e.g. vegetable oils, for example rapeseed oil, sunflower oil, mineral oils, for example paraffin oils, alkyl esters of vegetable fatty acids, for example rapeseed oil methyl ester or soybean oil methyl ester, or alkanol alkoxylates, and/or spreaders, for example alkylsiloxanes, and/or salts, for example organic or inorganic ammonium or phosphonium salts, for example ammonium sulfate or diammonium hydrogenphosphate, and/or retention promoters, for example dioctyl sulfosuccinate or hydroxypropyl guar polymers, and/or humectants, for example glycerol, and/or fertilizers, for example ammonium-, potassium- or phosphorus-containing fertilizers.

The formulations optionally comprise, as well as one or more inventive active ingredients, further active agrochemical ingredients.

These are preferably formulations or use forms which comprise auxiliaries, for example extenders, solvents, spontaneity promoters, carriers, emulsifiers, dispersants, antifreezes, biocides, thickeners and/or further auxiliaries, for example adjuvants. An adjuvant in this context is a component which enhances the biological effect of the formulation, without the component itself having any biological effect. Examples of adjuvants are agents which promote retention, spreading, adhesion to the leaf surface or penetration.

These formulations are produced in a known manner, for example by mixing the active ingredients with auxiliaries, for example extenders, solvents and/or solid carriers and/or further auxiliaries, for example surfactants. The formulations are produced either in suitable facilities or else before or during application.

The auxiliaries used may be substances suitable for imparting special properties, such as certain physical, technical and/or biological properties, to the formulation of the active ingredient, or to the use forms prepared from these formulations (for example ready-to-use crop protection compositions such as spray liquors or seed dressing products).

Suitable extenders are, for example, water, polar and nonpolar organic chemical liquids, for example from the classes of the aromatic and non-aromatic hydrocarbons (such as paraffins, alkylbenzenes, alkylnaphthalenes, chlorobenzenes), the alcohols and polyols (which may optionally also be substituted, etherified and/or esterified), the ketones (such as acetone, cyclohexanone), esters (including fats and oils) and (poly)ethers, the unsubstituted and substituted amines, amides, lactams (such as N-alkylpyrrolidones) and lactones, the sulfones and sulfoxides (such as dimethyl sulfoxide), and also N,N-dimethyldecanamide, N,N-dimethyloctanamide, N,N-dimethyldodedecanamide, Rhodiasolv Polarclean™ (methyl 5-(dimethylamino)-2-methyl-5-oxopentanoate).

If the extender utilized is water, it is also possible to use, for example, organic solvents as auxiliary solvents. Useful liquid solvents are essentially: aromatics such as xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example mineral oil fractions, mineral and vegetable oils, alcohols such as butanol or glycol and their ethers and esters, ketones such as acetone, methyl ethyl ketone, methyl isobutyl ketone or cyclohexanone, strongly polar solvents such as dimethylformamide and dimethyl sulfoxide, and also water.

In principle, it is possible to use all suitable solvents. Examples of suitable solvents are aromatic hydrocarbons, for example xylene, toluene or alkylnaphthalenes, chlorinated aromatic or chlorinated aliphatic hydrocarbons, for example chlorobenzene, chloroethylene or methylene chloride, aliphatic hydrocarbons, for example cyclohexane, paraffins, petroleum fractions, mineral and vegetable oils, alcohols, for example methanol, ethanol, isopropanol, butanol or glycol and the ethers and esters thereof, ketones, for example acetone, methyl ethyl ketone, methyl isobutyl ketone or cyclohexanone, strongly polar solvents such as dimethyl sulfoxide, and water.

In principle, it is possible to use all suitable carriers. Useful carriers include especially: for example ammonium salts and ground natural minerals such as kaolins, clays, talc, chalk, quartz, attapulgite, montmorillonite or diatomaceous earth, and ground synthetic materials such as finely divided silica, alumina and natural or synthetic silicates, resins, waxes and/or solid fertilizers. Mixtures of such carriers can likewise be used. Useful carriers for granules include: for example crushed and fractionated natural rocks such as calcite, marble, pumice, sepiolite, dolomite, and synthetic granules of inorganic and organic meals, and also granules of organic material such as sawdust, paper, coconut shells, corn cobs and tobacco stalks.

Liquefied gaseous extenders or solvents can also be used. Particularly suitable extenders or carriers are those which are gaseous at standard temperature and under standard pressure, for example aerosol propellant gases, such as halohydrocarbons, and also butane, propane, nitrogen and carbon dioxide.

Examples of emulsifiers and/or foam formers, dispersants or wetting agents with ionic or nonionic properties, or mixtures of these surfactants, include salts of polyacrylic acid, salts of lignosulfonic acid, salts of phenolsulfonic acid or naphthalenesulfonic acid, polycondensates of ethylene oxide with fatty alcohols or with fatty acids or with fatty amines, with substituted phenols (preferably alkylphenols or arylphenols), salts of sulfosuccinic esters, taurine derivatives (preferably alkyl taurates), phosphoric esters of polyethoxylated alcohols or phenols, fatty acid esters of polyols, and derivatives of the compounds containing sulfates, sulfonates and phosphates, for example alkylaryl polyglycol ethers, alkyl sulfonates, alkylsulfates, arylsulfonates, protein hydrolysates, lignosulfite waste liquors and methylcellulose. The presence of a surfactant is advantageous when one of the active ingredients and/or one of the inert carriers is insoluble in water and when application is effected in water.

Further auxiliaries which may be present in the formulations and the use forms derived therefrom include dyes such as inorganic pigments, for example iron oxide, titanium oxide and Prussian Blue, and organic dyes such as alizarin dyes, azo dyes and metal phthalocyanine dyes, and nutrients and trace nutrients such as salts of iron, manganese, boron, copper, cobalt, molybdenum and zinc.

Additional components may be stabilizers, such as cold stabilizers, preservatives, antioxidants, light stabilizers, or other agents which improve chemical and/or physical stability. Foam formers or antifoams may also be present.

In addition, the formulations and the use forms derived therefrom may also comprise, as additional auxiliaries, stickers such as carboxymethyl cellulose and natural and synthetic polymers in the form of powders, granules or latices, such as gum arabic, polyvinyl alcohol and polyvinyl acetate, or else natural phospholipids such as cephalins and lecithins and synthetic phospholipids. Further auxiliaries may be mineral and vegetable oils.

Optionally, further auxiliaries may be present in the formulations and the use forms derived therefrom. Examples of such additives include fragrances, protective colloids, binders, adhesives, thickeners, thixotropic agents, penetrants, retention promoters, stabilizers, sequestrants, complexing agents, humectants, spreaders. In general, the active ingredients can be combined with any solid or liquid additive which is commonly used for formulation purposes.

Useful retention promoters include all those substances which reduce the dynamic surface tension, for example dioctyl sulfosuccinate, or increase the viscoelasticity, for example hydroxypropylguar polymers.

Useful penetrants in the present context are all those substances which are typically used to improve the penetration of active agrochemical ingredients into plants. Penetrants are defined in this context by their ability to penetrate from the (generally aqueous) application liquor and/or from the spray coating into the cuticle of the plant and thereby increase the mobility of active ingredients in the cuticle. The method described in the literature (Baur et al., 1997, Pesticide Science 51, 131-152) can be used to determine this property. Examples include alcohol alkoxylates such as coconut fatty ethoxylate (10) or isotridecyl ethoxylate (12), fatty acid esters, for example rapeseed oil methyl ester or soya oil methyl ester, fatty amine alkoxylates, for example tallowamine ethoxylate (15), or ammonium and/or phosphonium salts, for example ammonium sulfate or diammonium hydrogenphosphate.

The formulations contain preferably between 0.00000001% and 98% by weight of active ingredient or more preferably between 0.01% and 95% by weight of active ingredient, more preferably between 0.5% and 90% by weight of active ingredient, based on the weight of the formulation.

The active ingredient content of the use forms (crop protection compositions) prepared from the formulations can vary within wide limits. The active ingredient concentration of the use forms may typically be between 0.00000001% and 95% by weight of active ingredient, preferably between 0.00001% and 1% by weight, based on the weight of the use form. Application is accomplished in a customary manner appropriate for the use forms.

The content of the individual components in the inventive formulations can be varied within a relatively wide range.

The inventive formulations are produced, for example, by mixing the components with one another in the particular ratios desired. If the active agrochemical ingredient is a solid substance, it is generally used either in finely ground form or in the form of a solution or suspension in an organic solvent or water. If the active agrochemical ingredient is liquid, there is frequently no need to use an organic solvent. It is also possible to use a solid active agrochemical ingredient in the form of a melt.

The temperatures can be varied within a particular range in the course of performance of the process. In general, working temperatures are between 0° C. and 80° C., preferably between 10° C. and 60° C.

In the performance of the process according to the invention, the procedure is generally to mix the N,N-dibutylcarboxamides of the formula (I) with one or more active ingredients and optionally with additives. The sequence in which the components are mixed with one another is arbitrary.

Useful equipment for performance of the process according to the invention is customary equipment which is used for production of agrochemical formulations.

Examples of administration forms include all the processes known as commonly used to the person skilled in the art: spraying, dipping, misting and a number of specific processes for direct treatment below or above ground of whole plants or parts (seed, root, stolons, stem, trunk, leaf), for example trunk injection in the case of trees or stem bandages in the case of perennial plants, and a number of specific indirect application processes.

The term "harmful organisms" encompasses all forms of organisms which cause economic and/or health damage in the particular field of use. Preference is given to organisms harmful to vegetables and animals, and to organisms which cause diseases, particular preference being given to terrestrial and aquatic weed grasses and broad-leaved weeds, algae, mosses, insects, mites, nematodes, rodents, fungi, bacteria and viruses.

The respective area- and/or object-based application rate of the crop protection compositions of a wide variety of different formulation types for control of the harmful organisms mentioned here varies very greatly. In general, the application media known to the person skilled in the art to be commonly used for the respective field of use are used for this purpose, for example several hundred liters of water per hectare in the case of standard spraying processes through a few liters of oil per hectare in the case of 'ultra low volume' aircraft application down to a few milliliters of a physiological solution in the case of injection processes. The concentrations of the inventive crop protection compositions in the particular application media therefore vary within a wide range and are dependent on the respective field of use. In general, concentrations known to the person skilled in the art to be commonly used for the respective field of use are used. Preferred concentrations are from 0.01% by weight to 99% by weight, more preferably from 0.1% by weight to 90% by weight.

The inventive crop protection compositions can be deployed, for example, in the formulation forms customary for liquid preparations, either as such or after prior dilution with water, i.e., for example, as emulsions, suspoemulsions, suspensions or solutions. Application is effected by customary methods, i.e., for example by spraying, pouring or injecting.

The application rate of the inventive crop protection compositions can be varied within a relatively wide range. It is guided by the active agrochemical ingredients in question and by the content thereof in the crop protection compositions.

According to the invention, it is possible to treat all plants and plant parts. Plants are understood here to mean all plants and plant populations, such as desired and undesired wild plants or crop plants (including naturally occurring crop plants). Crop plants may be plants which can be obtained by the conventional breeding and optimization methods or by biotechnological and genetic engineering methods or combinations of these methods, including the transgenic plants and including the plant cultivars which are protectable and non-protectable by plant breeders' rights. Plant parts are understood to mean all parts and organs of plants above and below the ground, such as shoot, leaf, flower and root, examples of which include leaves, needles, stalks, stems, flowers, fruit bodies, fruits and seeds, and also roots, tubers and rhizomes. Plant parts also include harvested material and vegetative and generative propagation material, for example cuttings, tubers, rhizomes, slips and seeds.

As already mentioned above, it is possible to treat all plants and parts thereof in accordance with the invention. In a preferred embodiment, wild plant species and plant cultivars, or those obtained by conventional biological breeding, such as crossing or protoplast fusion, and parts thereof, are treated. In a further preferred embodiment, transgenic plants and plant cultivars obtained by genetic engineering methods, if appropriate in combination with conventional methods (genetically modified organisms), and parts thereof are treated. The term "parts" or "parts of plants" or "plant parts" has been explained above. More preferably, plants of the plant cultivars which are commercially available or are in use are treated in accordance with the invention. Plant cultivars are understood to mean plants which have new properties ("traits") and have been obtained by conventional breeding, by mutagenesis or by recombinant DNA techniques. They may be cultivars, varieties, biotypes or genotypes.

The preferred transgenic plants or plant cultivars (those obtained by genetic engineering) which are to be treated in accordance with the invention include all plants which, through the genetic modification, received genetic material which imparts particular advantageous useful traits to these plants. Examples of such properties are better plant growth, increased tolerance to high or low temperatures, increased tolerance to drought or to levels of water or soil salinity, enhanced flowering performance, easier harvesting, accelerated ripening, higher yields, higher quality and/or a higher nutritional value of the harvested products, longer storage life and/or processability of the harvested products. Further and particularly emphasized examples of such properties are an improved defense of the plants against animal and microbial pests, such as against insects, mites, phytopathogenic fungi, bacteria and/or viruses, and also increased tolerance of the plants to certain herbicidally active ingredients. Examples of transgenic plants include the important crop plants, such as cereals (wheat, rice), maize, soybeans, potatoes, sugarbeet, tomatoes, peas and other vegetable types, cotton, tobacco, oilseed rape, and also fruit plants (with the fruits of apples, pears, citrus fruits and grapes), particular emphasis being given to maize, soybeans, potatoes, cotton, tobacco and oilseed rape. Traits that are particularly emphasized are improved defense of the plants against insects, arachnids, nematodes, slugs and snails by toxins formed in the plants, especially those formed in the plants by the genetic material from *Bacillus thuringiensis* (for example by the genes CryIA(a), CryIA(b), CryIA(c), CryIIA, CryIIIA, CryIIIB2, Cry9c, Cry2Ab, Cry3Bb and CryIF, and also combinations thereof) (referred to hereinafter as "Bt plants"). Traits that are also particularly emphasized are the improved defense of plants against fungi, bacteria and viruses by systemic acquired resistance (SAR), systemin, phytoalexins, elicitors and also resistance genes and correspondingly expressed proteins and toxins. Traits that are additionally particularly emphasized are the increased tolerance of the plants to certain active herbicidal ingredients, for example imidazolinones, sulfonylureas, glyphosate or phosphinothricin (for example the "PAT" gene). The genes which impart the desired traits in question can also be present in combinations with one another in the transgenic plants. Examples of "Bt plants" include maize varieties, cotton varieties, soya varieties and potato varieties which are sold under the trade names YIELD GARD® (for example maize, cotton, soya), KnockOut® (for example maize), StarLink® (for example maize), Bollgard® (cotton), Nucotn® (cotton) and NewLeaf® (potato). Examples of herbicide-tolerant plants which may be mentioned are maize varieties, cotton varieties and soybean varieties which are sold under the trade names Roundup Ready® (tolerance against glyphosate, for example maize, cotton, soybeans), Liberty Link® (tolerance against phosphinothricin, for example oilseed rape), IMI® (tolerance against imidazolinones) and STS® (tolerance against sulfonylurea, for example maize). Herbicide-resistant plants (plants bred in a conventional manner for herbicide tolerance) also include the varieties sold under the Clearfield® name (for example maize) Of course, these statements also apply to plant cultivars which have these genetic traits or genetic traits which are still to be developed and will be developed and/or marketed in the future.

Preferred plants are those from the group of the useful plants, ornamental plants, turfgrass types, commonly used trees which are employed as ornamentals in public and domestic areas, and forestry trees. Forestry trees include trees for the production of timber, cellulose, paper and products made from parts of the trees.

The term useful plants as used here refers to crop plants which are employed as plants for obtaining foods, animal feeds, fuels or for industrial purposes.

The useful plants which can be treated in accordance with the invention include, for example, the following plant species: turf, vines, cereals, for example wheat, barley, rye, oats, rice, maize and millet/sorghum; beet, for example sugar beet and fodder beet; fruits, for example pome fruit, stone fruit and soft fruit, for example apples, pears, plums, peaches, almonds, cherries and berries, for example strawberries, raspberries, blackberries; legumes, for example beans, lentils, peas and soybeans; oil crops, for example oilseed rape, mustard, poppies, olives, sunflowers, coconuts, castor oil plants, cacao beans and peanuts; cucurbits, for example pumpkin/squash, cucumbers and melons; fiber plants, for example cotton, flax, hemp and jute; citrus fruit, for example, oranges, lemons, grapefruit and tangerines; vegetables, for example spinach, lettuce, asparagus, cabbage species, carrots, onions, tomatoes, potatoes and bell peppers; Lauraceae, for example avocado, Cinnamomum, camphor, or also plants such as tobacco, nuts, coffee, aubergine, sugarcane, tea, pepper, grapevines, hops, bananas, latex plants and ornamentals, for example flowers, shrubs, deciduous trees and coniferous trees. This enumeration does not constitute a limitation.

The following plants are considered to be particularly suitable target crops for the application of the process according to the invention: cotton, aubergine, turf, pome fruit, stone fruit, soft fruit, maize, wheat, barley, cucumber, tobacco, vines, rice, cereals, pear, beans, soybeans, oilseed rape, tomato, bell pepper, melons, cabbage, potatoes and apples.

The plants treated in accordance with the invention are, where the use of herbicides is concerned, all kinds of weeds. With regard to the protection of crop plants through application of, for example, fungicides and insecticides, preference is given to application in economically important crops, for example including transgenic crops, of useful plants and ornamentals, for example of cereals such as wheat, barley, rye, oats, millet/sorghum, rice, manioc and corn, or else crops of sugar beet, cotton, soybean, oilseed rape, potato, tomato, peas and other vegetables.

The invention is illustrated in detail by the examples but is not restricted thereto.

PRODUCTION EXAMPLES

Penetration Test

In this test, the penetration of active ingredients though enzymatically isolated cuticles of apple tree leaves was measured. Leaves which had been cut off in the fully developed state from apple trees of the Golden Delicious variety were used. The cuticles were isolated by first filling leaf disks, which had been marked with dye on the underside and punched out, with a pectinase solution (0.2 to 2% strength) buffered to a pH between 3 and 4 by means of vacuum infiltration, then adding sodium azide and leaving the leaf disks thus treated to stand until the original leaf structure has dissolved and the non-cellular cuticle has become detached.

Thereafter, only the cuticles of the upper leaf sides which were free of stomata and hairs were used in the further procedure. They were repeatedly washed alternately with water and a buffer solution of pH 7. The clean cuticles obtained were finally applied to Teflon sheets and smoothed and dried with a gentle air stream.

In the next step, the cuticular membranes thus obtained were placed into stainless steel diffusion cells (=transport chambers) for membrane transport studies. For this purpose, the cuticles were positioned using tweezers centrally onto the edges of the diffusion cells which had been smeared with silicone grease and sealed with a ring which had likewise been greased. The arrangement was selected such that the morphological outer side of the cuticles was directed outward, i.e. toward the air, while the original inner side faced the interior of the diffusion cell. The diffusion cells were filled with water or with a mixture of water and solvent.

In the case of formulated samples, the active ingredients were made up in tap water and the test additive was added. When unformulated active ingredients were used, a mixture of acetone/tap water was used. The acetone contents varied between 20% (m/m) and 30% (m/m). This mixture was then added to the initial charge of additive/emulsifier mixture, which gave a transparent solution or an emulsion. In the cases where no solvent or emulsifier was used, an applicable emulsion has been produced by ultrasound homogenization.

To determine the penetration, 10 µl in each case of a spray liquor of the composition specified in the examples were applied to the outer side of a cuticle. After the application of the spray liquors, the water was allowed to vaporize in each case, then the chambers were turned round in each case and placed into thermostated tanks, while blowing air at a defined temperature and air humidity onto the outer side of the cuticle. The penetration which set in therefore took place at a relative air humidity of 60% and a set temperature of 25° C. The active ingredient penetration was measured by means of HPLC or radiolabeled active ingredient.

As is apparent from the examples listed in the table, the presence of N,N-dibutylcarboxamides leads to a distinct rise in the penetration of all the active ingredients tested. The control used here in each case was the variant without N,N-dibutylcarboxamides, which was either the active ingredient or the formulation alone, or else, when an emulsifier was used in the mixture with N,N-dibutylcarboxamide, the active ingredient or the formulation with this emulsifier.

The dimethyl- and dibutylcarboxamides used in the examples are the respective mixtures of the corresponding carboxamides. For example, C16-18 dibutyl amide means a mixture consisting essentially of N,N-dibutyl-C16- and -C18-carboxamides.

Table

Example 1

The bromoxynil active ingredient was made up formulated as WP 20 in tap water (1 g/l bromoxynil) and applied with castor oil ethoxylate emulsifier alone (0.5 g/l) or different spray liquor concentrations of N,N-dibutyl-C12-14-carboxamide (emulsified with a castor oil ethoxylate emulsifier), and the penetration of bromoxynil was measured. The table shows the penetration after 3 and 24 hours at 20° C. and 60% relative air humidity.

| bromoxynil WP20 without/with | Additive concentration (g/l) | Mean penetration of bromoxynil* in % (n = 4-8) | |
|---|---|---|---|
| | | 3 h | 24 h |
| bromoxynil WP20 in water without additive | — | 1 | 8 |
| castor oil ethoxylate emulsifier** | 0.5 | 1 | 12 |
| C12-14 dibutyl amide** | 1 | 5 | 25 |
| C12-14 dibutyl amide** | 3 | 6 | 23 |
| C12-14 dibutyl amide** | 5 | 5 | 26 |

*1.0 g/l bromoxynil;
**with 0.5 g/l castor oil ethoxylate as emulsifier

The addition of N,N-dibutyl-C12-14-carboxamide has led to a distinct rise, which has low dependence on concentration above 1 g/l, in the penetration of bromoxynil.

Table

Example 2

The bromoxynil octanoate active ingredient was made up formulated as EC225 in water (1.5 g/l bromoxynil octanoate) and applied with castor oil ethoxylate emulsifier alone (0.5 g/l) or different spray liquor concentrations of N,N-dibutyl-C12-14-carboxamide (emulsified with a castor oil ethoxylate emulsifier), and the penetration of bromoxynil octanoate was measured. The table shows the penetration after 3 and 24 hours at 20° C. and 60% relative air humidity.

| bromoxynil octanoate without/with | Additive concentration (g/l) | Mean penetration of bromoxynil octanoate* in % (n = 4-8) 3 h | 24 h |
|---|---|---|---|
| bromoxynil octanoate EC225 in water without additive | — | 5 | 49 |
| castor oil ethoxylate emulsifier** | 0.5 | 5 | 51 |
| C12-14 dibutyl amide** | 1 | 12 | 53 |
| C12-14 dibutyl amide** | 3 | 13 | 70 |
| C12-14 dibutyl amide** | 5 | 18 | 68 |

*1.5 g/l bromoxynil octanoate;
**with 0.5 g/l castor oil ethoxylate as emulsifier The addition of N,N-dibutyl-C12-14-carboxamide has led to a distinct, concentration-independent rise in the penetration of bromoxynil octanoate, particularly immediately after application.

Table

Example 3

The bromoxynil active ingredient was made up in acetone/water (1.5 g/l bromoxynil) and applied with castor oil ethoxylate emulsifier alone (0.5 g/l) or different spray liquor concentrations of N,N-dibutyl-C12-14-carboxamide (emulsified with a castor oil ethoxylate emulsifier), and the penetration of bromoxynil was measured. The table shows the penetration after 3 and 24 hours at 20° C. and 60% relative air humidity.

| bromoxynil without/with | Additive concentration (g/l) | Mean penetration of bromoxynil* in % (n = 4-8) 3 h | 24 h |
|---|---|---|---|
| castor oil ethoxylate emulsifier** | 0.5 | 1 | 9 |
| C12-14 dibutyl amide** | 1 | 29 | 70 |
| C12-14 dibutyl amide** | 3 | 59 | 85 |
| C12-14 dibutyl amide** | 5 | 61 | 83 |

*1.5 g/l bromoxynil;
**with 0.5 g/l castor oil ethoxylate as emulsifier

The addition of N,N-dibutyl-C12-14-carboxamide has led to a distinct, concentration-independent rise in the penetration of bromoxynil.

Table

Example 4

The bromoxynil active ingredient was made up in acetone/water (1.5 g/l bromoxynil) and applied with castor oil ethoxylate emulsifier alone (0.5 g/l) or different spray liquor concentrations of N,N-dibutyl-C8-10-carboxamide (emulsified with a castor oil ethoxylate emulsifier), and the penetration of bromoxynil was measured. The table shows the penetration after 3 and 24 hours at 20° C. and 60% relative air humidity.

| bromoxynil without/with | Additive concentration (g/l) | Mean penetration of bromoxynil* in % (n = 4-8) 3 h | 24 h |
|---|---|---|---|
| castor oil ethoxylate emulsifier** | 0.5 | 2 | 10 |
| C8-10 dibutyl amide** | 1 | 14 | 48 |
| C8-10 dibutyl amide** | 3 | 27 | 85 |
| C8-10 dibutyl amide** | 5 | 30 | 82 |

*1.5 g/l bromoxynil;
**with 0.5 g/l castor oil ethoxylate as emulsifier

The addition of N,N-dibutyl-C12-14-carboxamide has led to a distinct, concentration-independent rise in the penetration of bromoxynil.

Table

Example 5

The bromoxynil active ingredient was made up in acetone/water (1.5 g/l bromoxynil) and applied with castor oil ethoxylate emulsifier (0.5 g/l) alone or together with N,N-dibutyl-C8-10-carboxamide, N,N-dibutyl-C12-14-carboxamide or N,N-dibutyl-C16-18-carboxamide (emulsified with a castor oil ethoxylate emulsifier) at a spray liquor concentration of 3 g/l, and the penetration of bromoxynil was measured. The table shows the penetration after 3 and 24 hours at 20° C. and 60% relative air humidity.

| bromoxynil without/with | Additive concentration (g/l) | Mean penetration of bromoxynil* in % (n = 4-8) 3 h | 24 h |
|---|---|---|---|
| castor oil ethoxylate emulsifier** | 0.5 | 1 | 6 |
| C8-10 dibutyl amide** | 3 | 16 | 39 |
| C12-14 dibutyl amide** | 3 | 8 | 31 |
| C16-18 dibutyl amide** | 3 | 7 | 32 |

*1.5 g/l bromoxynil;
**with 0.5 g/l castor oil ethoxylate as emulsifier

The addition of the N,N-dibutylcarboxamides has led to a distinct rise in the penetration of bromoxynil.

Table

Example 6

The bromoxynil active ingredient was made up in acetone/water (1.5 g/l bromoxynil) and applied with castor oil ethoxylate emulsifier (0.5 g/l) alone or together with noninventive N,N-dimethyl-C8-C10-carboxamide or inventive N,N-dibutyl-C8-C10-carboxamide or N,N-dibutyl-C12-C14-carboxamide (emulsified with a castor oil ethoxylate emulsifier) at a spray liquor concentration of 1 or 3 g/l, and the penetration of bromoxynil was measured. The table shows the penetration after 5 and 24 hours at 20° C. and 60% relative air humidity.

| bromoxynil variant without/with | N,N-dialkylcarboxamide concentration (g/l) | Mean penetration of bromoxynil* in % (n = 4-8) 5 h | 24 h |
|---|---|---|---|
| bromoxynil in acetone/water with 0.5 g/l castor oil ethoxylate emulsifier | — | 4 | 20 |

-continued

| bromoxynil variant without/with | N,N-dialkylcarboxamide concentration (g/l) | Mean penetration of bromoxynil* in % (n = 4-8) | |
|---|---|---|---|
| | | 5 h | 24 h |
| C8-10 dimethyl amide** | 1 | 20 | 30 |
| C8-10 dimethyl amide** | 3 | 45 | 57 |
| C8-10 dibutyl amide** | 1 | 32 | 72 |
| C8-10 dibutyl amide** | 3 | 67 | 86 |
| C12-14 dibutyl amide** | 1 | 29 | 70 |
| C12-14 dibutyl amide** | 3 | 59 | 85 |

*1.5 g/l bromoxynil
**with 0.5 g/l castor oil ethoxylate emulsifier

The addition of the N,N-dibutylcarboxamides has led to a distinct, concentration-independent rise in the penetration of bromoxynil. In all cases, the effect was distinctly superior to that of the dimethyl-C8-C10-carboxamides.

Table

Example 7

The spirotetramat active ingredient was dissolved in acetone/water (0.3 g/l spirotetramat) and applied alone or together with different spray liquor concentrations of N,N-dibutyl-C12-14-carboxamide (emulsified with a castor oil ethoxylate emulsifier), and the penetration of spirotetramat was measured. The table shows the penetration after 3 and 24 hours at 20° C. and 60% relative air humidity.

| spirotetramat without/with | N,N-dibutylcarboxamide concentration | Mean penetration of spirotetramat* in % (n = 4-8) | |
|---|---|---|---|
| | | 3 h | 24 h |
| spirotetramat in acetone/water without N,N-dibutylcarboxamide | — | 0 | 1 |
| C12-14 dibutyl amide** | 0.2 | 2 | 23 |
| C12-14 dibutyl amide** | 0.5 | 2 | 25 |
| C12-14 dibutyl amide** | 1 | 8 | 39 |
| C12-14 dibutyl amide** | 3 | 13 | 65 |

*0.3 g/l spirotetramat;
**with 0.5 g/l castor oil ethoxylate as emulsifier

The addition of N,N-dibutyl-C12-14-carboxamide has led to a distinct, concentration-independent rise in the penetration of spirotetramat.

Table

Example 8

The spirotetramat active ingredient was made up formulated as SC240 in tap water (0.3 g/l spirotetramat) and applied alone or together with N,N-dibutyl-C8-10-carboxamide, N,N-dibutyl-C12-14-carboxamide or N,N-dibutyl-C16-18-carboxamide at a spray liquor concentration of 1 g/l (homogenized by ultrasound treatment), and the penetration of spirotetramat was measured. The table shows the penetration after 3 and 24 hours at 20° C. and 60% relative air humidity.

| spirotetramat without/with | N,N-dibutyl-carboxamide concentration (g/l) | Mean penetration of spirotetramat* in % (n = 4-8) | |
|---|---|---|---|
| | | 3 h | 24 h |
| spirotetramat SC240 without N,N-dibutyl-carboxamide | — | 1 | 2 |
| C8-10 dibutyl amide | 1 | 11 | 13 |
| C12-14 dibutyl amide | 1 | 4 | 10 |
| C16-18 dibutyl amide | 1 | 4 | 16 |

*0.3 g/l spirotetramat

The addition of the three N,N-dibutylcarboxamides has led to a distinct rise in the penetration of spirotetramat.

Table

Example 9

The kresoxim-methyl active ingredient was made up in acetone/tap water (0.3 g/l kresoxim-methyl) and applied alone or together with N,N-dibutyl-C8-10-carboxamide, N,N-dibutyl-C12-14-carboxamide or N,N-dibutyl-C16-18-carboxamide at a spray liquor concentration of 1 or 3 g/l (emulsified with 0.4 g/l tristyrylphenyl ethoxylate), and the penetration of kresoxim-methyl was measured. The table shows the penetration after 3 and 24 hours at 20° C. and 60% relative air humidity.

| kresoxim-methyl | N,N-dibutyl-carboxamide concentration (g/l) | Mean penetration of kresoxim-methyl * in % (n = 4-8) | |
|---|---|---|---|
| | | 3 h | 24 h |
| kresoxim-methyl in acetone/water without N,N-dibutylcarboxamide | — | 1 | 3 |
| C8-10 dibutyl amide** | 3 | 60 | 66 |
| C12-14 dibutyl amide** | 1 | 51 | 82 |
| C12-14 dibutyl amide** | 3 | 68 | 99 |
| C16-18 dibutyl amide** | 3 | 52 | 76 |

* 0.3 g/l kresoxim-methyl,
**with 0.4 g/l tristyrylphenol ethoxylate

The addition of the three N,N-dibutylcarboxamides has led to a distinct rise in the penetration of kresoxim-methyl.

Table

Example 10

The azoxystrobin active ingredient was made up in acetone/tap water (0.3 g/l azoxystrobin) and applied alone or together with N,N-dibutyl-C8-10-carboxamide, N,N-dibutyl-C12-14-carboxamide or N,N-dibutyl-C16-18-carboxamide at a spray liquor concentration of 1 or 3 g/l (emulsified with 0.4 g/l tristyrylphenyl ethoxylate), and the penetration of azoxystrobin was measured. The table shows the penetration after 3 and 24 hours at 20° C. and 60% relative air humidity.

| azoxystrobin variant | N,N-dibutyl-carboxamide | Mean penetration of azoxystrobin * in % (n = 4-8) | |
|---|---|---|---|
| without/with | concentration (g/l) | 3 h | 24 h |
| azoxystrobin in acetone/water without N,N-dibutylcarboxamide | — | <1 | 1 |
| C8-10 dibutyl amide** | 3 | 34 | 46 |
| C12-14 dibutyl amide** | 1 | 7 | 14 |
| C12-14 dibutyl amide** | 3 | 9 | 37 |
| C16-18 dibutyl amide** | 3 | 6 | 36 |

* 0.3 g/l azoxystrobin,
**with 0.4 g/l tristyrylphenol ethoxylate

The addition of the three N,N-dibutylcarboxamides has led to a distinct rise in the penetration of azoxystrobin.

Table

Example 11

The epoxiconazole active ingredient was made up in acetone/tap water (0.3 g/l epoxiconazole) and applied alone or together with N,N-dibutyl-C8-10-carboxamide, N,N-dibutyl-C12-14-carboxamide or N,N-dibutyl-C16-18-carboxamide at a spray liquor concentration of 1 or 3 g/l (emulsified with 0.4 g/l tristyrylphenyl ethoxylate), and the penetration of epoxiconazole was measured. The table shows the penetration after 3 and 24 hours at 20° C. and 60% relative air humidity.

| epoxiconazole variant | N,N-dibutyl-carboxamide | Mean penetration of epoxiconazole * in % (n = 4-8) | |
|---|---|---|---|
| without/with | concentration (g/l) | 3 h | 24 h |
| epoxiconazole in acetone/water without N,N-dibutylcarboxamide | — | 1 | 2 |
| C8-10 dibutyl amide** | 3 | 67 | 73 |
| C12-14 dibutyl amide** | 1 | 52 | 96 |
| C12-14 dibutyl amide** | 3 | 54 | 95 |
| C16-18 dibutyl amide** | 3 | 17 | 95 |

* 0.3 g/l epoxiconazole,
**with 0.4 g/l tristyrylphenol ethoxylate

The addition of the three N,N-dibutylcarboxamides has led to a distinct rise in the penetration of epoxiconazole.

Table

Example 12

The propiconazole active ingredient was made up in acetone/tap water (0.3 g/l propiconazole) and applied alone or together with N,N-dibutyl-C12-14-carboxamide or N,N-dibutyl-C16-18-carboxamide at a spray liquor concentration of 1 or 3 g/l (emulsified with 0.4 g/l tristyrylphenyl ethoxylate), and the penetration of propiconazole was measured. The table shows the penetration after 3 and 24 hours at 20° C. and 60% relative air humidity.

| propiconazole variant | N,N-dibutyl-carboxamide | Mean penetration of propiconazole * in % (n = 4-8) | |
|---|---|---|---|
| without/with | concentration (g/l) | 3 h | 24 h |
| propiconazole in acetone/water without N,N-dibutylcarboxamide | — | 4 | 44 |
| C12-14 dibutyl amide** | 1 | 53 | 85 |
| C12-14 dibutyl amide** | 3 | 72 | 89 |
| C16-18 dibutyl amide** | 3 | 45 | 92 |

* 0.3 g/l propiconazole,
**with 0.4 g/l tristyrylphenol ethoxylate

The addition of N,N-dibutyl-C12-14-carboxamide or N,N-dibutyl-C16-18-carboxamide has led to a distinct rise in the penetration of propiconazole.

Table

Example 13

The isopyrazam active ingredient was made up in acetone/tap water (0.3 g/l isopyrazam) and applied alone or together with N,N-dibutyl-C8-10-carboxamide, N,N-dibutyl-C12-14-carboxamide or N,N-dibutyl-C16-18-carboxamide at a spray liquor concentration of 1 or 3 g/l (emulsified with 0.4 g/l tristyrylphenyl ethoxylate), and the penetration of isopyrazam was measured. The table shows the penetration after 3 and 24 hours at 20° C. and 60% relative air humidity.

| isopyrazam variant | N,N-dibutyl-carboxamide | Mean penetration of isopyrazam * in % (n = 4-8) | |
|---|---|---|---|
| without/with | concentration (g/l) | 3 h | 24 h |
| isopyrazam in acetone/water without N,N-dibutylcarboxamide | — | 1 | 2 |
| C8-10 dibutyl amide** | 3 | 37 | 87 |
| C12-14 dibutyl amide** | 1 | 11 | 54 |
| C12-14 dibutyl amide** | 3 | 12 | 49 |
| C16-18 dibutyl amide** | 3 | 10 | 35 |

* 0.3 g/l isopyrazam,
**with 0.4 g/l tristyrylphenol ethoxylate

The addition of the three N,N-dibutylcarboxamides has led to a distinct rise in the penetration of isopyrazam.

Table

Example 14

The indaziflam active ingredient (formulated as SC500) was made up in tap water (0.3 g/l indaziflam) and applied alone or together with N,N-dibutyl-C8-10-carboxamide, N,N-dibutyl-C12-14-carboxamide or N,N-dibutyl-C16-18-carboxamide at a spray liquor concentration of 2.5 g/l (emulsified with castor oil ethoxylate or tristyrylphenol ethoxylates), and the penetration of indaziflam was measured. The table shows the penetration after 24 and 48 hours at 20° C. and 60% relative air humidity.

| indaziflam variant | N,N-dibutyl-carboxamide | Mean penetration of indaziflam * in % (n = 4-8) | |
|---|---|---|---|
| without/with | concentration (g/l) | 24 h | 48 h |
| indaziflam SC500 in water without N,N-dibutylcarboxamide | — | 3 | 6 |
| C8-10 dibutyl amide** | 2.5 | 26 | 34 |
| C12-14 dibutyl amide** | 2.5 | 27 | 49 |
| C16-18 dibutyl amide** | 2.5 | 8 | 17 |
| C16-18 dibutyl amide*** | 2.5 | 14 | 70 |
| C16-18 dibutyl amide**** | 2.5 | 40 | 77 |

* 0.3 g/l indaziflam,
**with 0.5 g/l castor oil ethoxylate as emulsifier,
*with 0.5 g/ tristyrylphenol ethoxylate 16 (*) or 29 EO (****)

The addition of the three N,N-dibutylcarboxamides has led to a distinct rise in the penetration of indaziflam.

Table

Example 15

The prothioconazole active ingredient was made up in acetone/tap water (0.3 g/l prothioconazole) and applied alone or together with N,N-dibutyl-C12-14-carboxamide or N,N-dibutyl-C16-18-carboxamide at a spray liquor concentration of 1 g/l (emulsified by ultrasound treatment), and the penetration of prothioconazole was measured. The table shows the penetration after 3 and 24 hours at 25° C. and 60% relative air humidity.

| prothioconazole variant | N,N-dibutyl-carboxamide | Mean penetration of prothioconazole* in % (n = 4-8) | |
|---|---|---|---|
| without/with | concentration (g/l) | 3 h | 24 h |
| prothioconazole in acetone/water | — | 1 | 2 |
| C12-14 dibutyl amide | 1 | 1 | 11 |
| C16-18 dibutyl amide | 1 | 5 | 18 |

*0.3 g/l prothioconazole

The addition of the two N,N-dibutylcarboxamides has led to a distinct rise in the penetration of prothioconazole.

Table

Example 16

Comparison of the N,N-Dibutylcarboxamides Used in Accordance with the Invention with the N,N-Dimethylcarboxamide from the Prior Art The table which follows shows the comparison of the penetration of prothioconazole from the commercial formulation or of a novel inventive composition where 20% of the N,N-dimethyl-C8-10-carboxamide solvent has been replaced by N,N-dibutyl-C16-18-carboxamide (figures in percent by mass), with 25% prothioconazole.
Formulation A:
20% KS emulsifier
20% N,N-dibutyl-C16-18-carboxamide
34.9% N,N-dibutyl-C8-10-carboxamide
0.1% defoamer
The prothioconazole active ingredient was made up formulated as the commercial standard EC250 or with the inventive formulation in tap water (0.3 g/l prothioconazole), and the penetration of prothioconazole was measured in an experiment in which 15° C. and 80% relative air humidity were set on the first day, and 25° and 60% on the second day. The table shows the penetration after 12 and 24 hours at 25° C. and 60% relative air humidity.

| | Mean penetration of prothioconazole* in % (n = 4-8) | | | |
|---|---|---|---|---|
| Variant | 12 h | 24 h | 36 h | 48 h |
| Standard EC250 formulation | 3 | 4 | 6 | 8 |
| Inventive EC250 formulation A | 6 | 10 | 19 | 23 |

*0.3 g/l prothioconazole

The example shows that the N,N-dibutylcarboxamides used in accordance with the invention lead to enhanced penetration compared to the N,N-dimethylcarboxamide from the prior art.

Table

Example 17

Comparison of the N,N-Dibutylcarboxamides Used in Accordance with the Invention with the N,N-Dimethylcarboxamide from the Prior Art The prothioconazole active ingredient was made up in acetone/tap water (0.8 g/l prothioconazole) and applied together with N,N-dimethyl-C8-10-carboxamide (1.5 g/l) alone or with addition (0.5 g/l or 1 g/l in the mixture) of inventive N,N-dibutyl-C8-10-carboxamide, N,N-dibutyl-C12-14-carboxamide or N,N-dibutyl-C16-18-carboxamide (in each case with 0.4 g/l tristyrylphenol ethoxylate), and the penetration of prothioconazole was measured. The table shows the penetration after 3 and 24 hours at 20° C. and 60% relative air humidity.

| prothioconazole variant | N,N-dibutyl-carboxamide | Mean penetration of prothioconazole* in % (n = 4-8) | |
|---|---|---|---|
| without/with | concentration (g/l) | 3 h | 24 h |
| Prothioconazole in acetone/water with 1.5 g/l N,N-dimethyl-C8-C10-carboxamide** | — | 1.3 (n = 21) | 3.7 (n = 21) |
| C8-10 dibutyl amide** | 0.5 | 2.1 | 6.3 |
| C8-10 dibutyl amide** | 1 | 2.5 | 9.3 |
| C12-14 dibutyl amide** | 0.5 | 2.0 | 9.4 |
| C12-14 dibutyl amide** | 1 | 4.2 | 16.6 |
| C16-18 dibutyl amide** | 0.5 | 2.1 | 7.4 |
| C16-18 dibutyl amide** | 1 | 3.2 | 17.9 |

*0.8 g/l prothioconazole,
**with 0.4 g/l tristyrylphenol ethoxylate

The addition of the three N,N-dibutylcarboxamides to a solution of prothioconazole already containing a relatively high amount of N,N-dimethyl-C8-C10-carboxamide has led to a distinct, more significant and concentration-dependent rise in the penetration of prothioconazole.

Example 18

Enhancement of the Fungicidal Action of Proline in Wheat with N,N-Dibutyl-C16-18-Carboxamide In two field trials, the influence of N,N-dibutyl-C16-18-carboxamide on the fungicidal efficacy of Proline EC250 against several pathogenic harmful fungi was tested. The field trials were set up in winter wheat in a field near Burscheid, Germany. The trials were randomized with three repetitions, and one trial plot had an area of 6 m². The planting dates were Oct. 20, 2009 and Oct. 21, 2009. Other fertilization and crop protection measures were in accordance with agricultural practice.

The test substances were applied twice in succession at the wheat growth stages EC32 and EC39. The interval was 2 or 3 weeks. Prothioconazole was used in the form of an EC 250 formulation (trade name: Proline), and the N,N-dibutyl-C16-18-carboxamide in the form of an EC500. Proline was used either alone or with tankmix addition of N,N-dibutyl-C16-18-carboxamide. The water application rate in the spray application was 300 l/ha.

The level of disease on the ears of wheat and the disease control (action) were rated on Jun. 30 and Jul. 1, 2010, i.e. about 4 weeks after the second fungicide application. The influence of N,N-dibutyl-C16-18-carboxamide on the enhancement of efficacy of Proline is shown in the table below.

| Variant | Pathogen Amount of active ingredient per hectare | Trial 1 *Leptosphaeria nodorum* | Trial 1 *Puccina recondita* | Trial 2 *Pyrenophora teres* |
|---|---|---|---|---|
| | | Action as per Abbott (%) | | |
| Untreated (infestation) | — | 14 | 5 | 5 |
| Proline | 75 | 67 | 72 | 70 |
| Proline + 0.1% N,N-dibutyl-C16-18-carboxamide * | 75 | 85 | 99 | 91 |

* 0.2% N,N-dibutyl-C16-18-carboxamide EC500 is an N,N-dibutyl-C16-18-carboxamide The result shows that even a concentration of 0.1% N,N-dibutyl-C16-18-carboxamide significantly enhances the fungicidal action of Proline.

Example 19

Enhancement of the Herbicidal Efficacy of Indaziflam with N,N-Dibutyl-C12-14-Carboxamide Two field trials were conducted in order to study the influence of C12-14 dibutyl amide on the herbicidal efficacy of the herbicide indaziflam. The field trials were set up (1) in Fresno (California, USA) and (2) Mereville (France). The two products were deployed on a natural mixture of weeds. The plot size in trial 1 was 9.3 m² and that in trial 2 was 6 m². The weed plants were treated with the products at an early development stage (the plant height measured according to the weed species was 2 cm to 7 cm). For this purpose, the products to be applied were dissolved and diluted in water and then sprayed with 187 liters per hectare (trial 1) and 250 liters per hectare (trial 2) as a spray solution directly onto the weed plants.

In both field trials, indaziflam SC500 as a single product was tested in comparison to indaziflam SC500 in a tankmix with 0.5 liter per hectare of N,N-dibutyl-C12-14-carboxamide. In trial 1, the application rate of indaziflam (formulated as SC500) was 50 grams of active substance per hectare, and in trial 2 it was 75 grams of active substance per hectare. The weed mixture consisted of the following monocotyledonous weeds: *Digitaria sanguinalis* (DIGSA), *Lolium multiflorum* (LOLMU), *Setaria glauca* (PESGL) and *Setaria verticillata* (SETVE), and of the following dicotyledonous weeds: *Amaranthus retroflexus* (AMARE), *Abutilon theophrasti* (ABUTH), *Chenopodium album* (CHEAL), *Fallopia convolvulus* (POLCO).

The herbicidal action of the products was rated visually compared to the untreated control. The herbicidal action was expressed in percent (%): 100% herbicidal action=weed plants have died off completely; 0% action=like control plants). Trial 1 was rated 7 days after the application of the products, and trial 2 was rated 28 days after the application. The respective results of the field trials are shown in table 1 (field trial 1) and in table 2 (field trial 2).

TABLE 19a

| Weed control as per Abbott (%) | Amount of active per ingredient hectare (g/ha) | AMARE | CHEAL | PESGL | LOLMU | ABUTH |
|---|---|---|---|---|---|---|
| indaziflam | 50 | 46 | 28 | 43 | 53 | 55 |
| indaziflam + C12-14 dibutyl amide | 50 | 88 | 73 | 82 | 83 | 85 |

TABLE 19b

| Weed control as per Abbott (%) | Amount of active ingredient per hectare (g/ha) | POLCO | CHEAL | SETVE | DIGSA |
|---|---|---|---|---|---|
| indaziflam | 75 | 15 | 10 | 45 | 15 |
| indaziflam + C12-14 dibutyl amide | 75 + 0.5 l/ha | 63 | 86 | 55 | 80 |

In both field trials, it was shown that the addition of 0.5 liter per hectare of N,N-dibutyl-C12-14-carboxamide to the indaziflam herbicide significantly enhances the efficacy on weeds.

Example 20

Coverage

It has also been found that, surprisingly, the water-insoluble N,N-dibutylcarboxamides distinctly increase the coverage—the proportion of the plant surface wetted with the spray liquid in the spray application—after emulsion with various emulsifiers. For instance, in the case of spray application with an air injector nozzle (TeeJet AI11003, 200 l/ha) to maize with 2 g/l of an emulsion of N,N-dibutyl-C12-14-carboxamide or N,N-dibutyl-C16-18-carboxamide (emulsified with 0.5 g/l sorbitan ester ethoxylate), the coverage was from 1.1% (proportion of the area wetted in relation to the plant area treated) for water to 18.5% (N,N-dibutyl-C12-14-carboxamide) or 17.9% (N,N-dibutyl-C16-18-carboxamide). The value for the emulsifier alone was 7.3%.

Table

Example 21

The active ingredient fluopyram was made up as an EC formulation in the laboratory: fluopyram is dissolved in a preliminary mixture of solvent and emulsifier (dimethylacetamide+Tanemul PS16) and diluted with water to give the ready-to-use test solution. The test solution contains 0.5 g/l active ingredient, 0.5 g/l emulsifier and 2% by weight of solvent. It is applied alone or together with N,N-dibutyl-C16-18-carboxamide or N,N-dimethyl-C18-carboxamide at a spray liquor concentration of 1.5 g/l (emulsified by ultrasound treatment) to isolated apple leaf cuticles and the penetration of fluopyram is measured. The table shows the penetration after 6 and 24 hours at 25° C. and 60% relative air humidity.

| Test solution | Carboxamide concentration (g/l) | Mean penetration of fluopyram in % ($n = 8$-$10$) | |
|---|---|---|---|
| | | 6 h | 24 h |
| fluopyram (0.5 g/l) | — | 20 | 53 |
| fluopyram & C16-18 dibutyl amide | 1.5 | 84 | 95 |
| fluopyram & C18 dimethyl amide | 1.5 | 34 | 51 |

The addition of the N,N-dibutyl-C16-C18-carboxamide compared to the corresponding dimethyl amide led to more significant enhancement of the penetration of fluopyram.

Table

Example 22

Intrinsic Penetration of the N,N-Dibutylcarboxamides

The N,N-dibutyl-C16-C18- and -C12-C14-alkyl/alkenyl-carboxamides and the analogous dimethyl amides were made up as EC formulations in the laboratory: they are dissolved in a preliminary mixture of solvent and emulsifier (dimethylacetamide+Tanemul PS16) and diluted with water to give the ready-to-use test solution (emulsified by ultrasound treatment). The test solutions each contain 1.5 g/l carboxamide, 0.5 g/l emulsifier and 2% by weight of solvent. They are applied to isolated apple leaf cuticles and then the intrinsic penetration of the carboxamides is measured. The table shows the penetration after 6 and 24 hours at 25° C. and 60% relative air humidity.

| Test solution | Carboxamide concentration (g/l) | Penetration of carboxamide in % ($n = 8$-$10$) | |
|---|---|---|---|
| | | 6 h | 24 h |
| C16-18 dibutyl amide | 1.5 | 0 | 0 |
| C18 dimethyl amide | 1.5 | 22 | 61 |
| C12-14 dibutyl amide | 1.5 | 2 | 4 |
| C12 dimethyl amide | 1.5 | 49 | 47 |

The intrinsic penetration of the N,N-dimethylcarboxamides is much greater than that of the analogous dibutyl amides. The C16-18 dibutyl amide has no measurable penetration at all.

FORMULATION EXAMPLES

The inventive formulations which follow were produced by mixing the individual components.

Formulation Example 1

To produce the proper invention with the active ingredient tebuconazole, the following are first mixed at room temperature with stirring:
20 g of tebuconazole with
56 g of N,N-dimethyldecanamide and then with
10 g of ethoxypropoxytristyrylphenol (block copolymer),
4 g of water and
10 g of N,N-dibutyl-C16-C18-carboxamide.
After addition has ended, the mixture is stirred at room temperature for a further 4 hours. In this way, a homogeneous solution is obtained.

Formulation Example 2

To produce the proper invention with the active ingredient tebuconazole, the following are first mixed at room temperature with stirring:
20 g of tebuconazole with
51 g of N,N-dimethyldecanamide and then with
10 g of ethoxypropoxytristyrylphenol (block copolymer),
4 g of water and
15 g of N,N-dibutyl-C16-C18-carboxamide.
After addition has ended, the mixture is stirred at room temperature for a further 4 hours. In this way, a homogeneous solution is obtained.

Formulation Example 3

To produce the proper invention with the active ingredient tebuconazole, the following are first mixed at room temperature with stirring:
20 g of tebuconazole with
52 g of N,N-dimethyldecanamide and then with
3 g of ethoxypropoxytristyrylphenol (block copolymer),
10 g of castor oil polyglycol ether ester and
15 g of N,N-dibutyl-C16-C18-carboxamide.
After addition has ended, the mixture is stirred at room temperature for a further 4 hours. In this way, a homogeneous solution is obtained.

Formulation Example 4

To produce the proper invention with the active ingredient epoxiconazole, the following are first mixed at room temperature with stirring:

10 g of epoxiconazole with
65 g of benzyl alcohol and then with
7.5 g of ethoxypropoxytristyrylphenol (block copolymer),
7.5 g of castor oil polyglycol ether ester and
10 g of N,N-dibutyl-C16-C18-carboxamide.

After addition has ended, the mixture is stirred at room temperature for a further 4 hours. In this way, a homogeneous solution is obtained.

Formulation Example 5

To produce the proper invention with the active ingredient epoxiconazole, the following are first mixed at room temperature with stirring:
10 g of epoxiconazole with
50 g of benzyl alcohol and then with
10 g of 2-sec-butylphenol,
7.5 g of ethoxypropoxytristyrylphenol (block copolymer),
7.5 g of castor oil polyglycol ether ester and
15 g of N,N-dibutyl-C16-C18-carboxamide.

After addition has ended, the mixture is stirred at room temperature for a further 4 hours. In this way, a homogeneous solution is obtained.

Formulation Example 6

To produce the proper invention with the active ingredient fluoxastrobin, the following are first mixed at room temperature with stirring:
10 g of fluoxastrobin with
35 g of gamma-butyrolactone and then with
15 g of 2-ethylhexanol propylene/ethylene glycol ether,
15 g of ethoxypropoxytristyrylphenol (block copolymer),
10 g of alkoxylated ethylenediamine having an average of 16 EO and 16 PO units,
5 g of tristyrylphenol ethoxylate having an average of 16 EO units and
10 g of N,N-dibutyl-C16-C18-carboxamide.

After addition has ended, the mixture is stirred at room temperature for a further 4 hours. In this way, a homogeneous solution is obtained.

Formulation Example 7

To produce the proper invention with the active ingredient fluoxastrobin, the following are first mixed at room temperature with stirring:
10 g of fluoxastrobin with
30 g of gamma-butyrolactone and then with
15 g of 2-ethylhexanol propylene/ethylene glycol ether,
15 g of ethoxypropoxytristyrylphenol (block copolymer),
10 g of alkoxylated ethylenediamine having an average of 16 EO and 16 PO units,
5 g of tristyrylphenol ethoxylate having an average of 16 EO units and
15 g of N,N-dibutyl-C16-C18-carboxamide.

After addition has ended, the mixture is stirred at room temperature for a further 4 hours. In this way, a homogeneous solution is obtained.

Formulation Example 8

To produce the proper invention with the active ingredient azoxystrobin, the following are first mixed at room temperature with stirring:
10 g of azoxystrobin with
35 g of gamma-butyrolactone and then with
15 g of 2-ethylhexanol propylene/ethylene glycol ether,
15 g of ethoxypropoxytristyrylphenol (block copolymer),
10 g of alkoxylated ethylenediamine having an average of 16 EO and 16 PO units,
5 g of tristyrylphenol ethoxylate having an average of 16 EO units and
10 g of N,N-dibutyl-C16-C18-carboxamide.

After addition has ended, the mixture is stirred at room temperature for a further 4 hours. In this way, a homogeneous solution is obtained.

Formulation Example 9

To produce the proper invention with the active ingredient azoxystrobin, the following are first mixed at room temperature with stirring:
10 g of azoxystrobin with
30 g of gamma-butyrolactone and then with
15 g of 2-ethylhexanol propylene/ethylene glycol ether,
15 g of ethoxypropoxytristyrylphenol (block copolymer),
10 g of alkoxylated ethylenediamine having an average of 16 EO and 16 PO units,
5 g of tristyrylphenol ethoxylate having an average of 16 EO units and
15 g of N,N-dibutyl-C16-C18-carboxamide.

After addition has ended, the mixture is stirred at room temperature for a further 4 hours. In this way, a homogeneous solution is obtained.

Formulation Example 10

To produce the proper invention with the active ingredient trifloxystrobin, the following are first mixed at room temperature with stirring:
10 g of trifloxystrobin with
44.97 g of N-methylpyrrolidone and then with
10 g of tristyrylphenol ethoxylate having an average of 16 EO units,
2.5 g of tristyrylphenol ethoxylate salt having an average of 16 EO units,
12.5 g of butoxypolyethylene-propylene glycol (block copolymer),
0.03 g of silicone antifoam emulsion and
20 g of N,N-dibutyl-C16-C18-carboxamide.

After addition has ended, the mixture is stirred at room temperature for a further 4 hours. In this way, a homogeneous solution is obtained.

Formulation Example 11

To produce the proper invention with the active ingredient prothioconazole, the following are first mixed at room temperature with stirring:
25 g of prothioconazole with
34.9 g of N,N-dimethyldecanamide and then with
20 g of castor oil polyglycol ether ester,
0.1 g of silicone antifoam emulsion and
20 g of N,N-dibutyl-C16-C18-carboxamide.

After addition has ended, the mixture is stirred at room temperature for a further 4 hours. In this way, a homogeneous solution is obtained.

Formulation Example 12

To produce the proper invention with the active ingredient prothioconazole, the following are first mixed at room temperature with stirring:

25 g of prothioconazole with
39.9 g of N,N-dimethyldecanamide and then with
10 g of ethoxypropoxytristyrylphenol (block copolymer),
10 g of tristyrylphenol ethoxylate having an average of 16 EO units and
0.1 g of silicone antifoam emulsion and
15 g of N,N-dibutyl-C16-C18-carboxamide.

After addition has ended, the mixture is stirred at room temperature for a further 4 hours. In this way, a homogeneous solution is obtained.

Formulation Example 13

To produce the proper invention with the active ingredient bixafen, the following are first mixed at room temperature with stirring:
10 g of bixafen with
45 g of N,N-dimethyldecanamide and then with
10 g of aromatic hydrocarbon mixture, naphthalene-reduced,
10 g of 2-ethylhexanol propylene/ethylene glycol ether,
10 g of castor oil polyglycol ether ester,
5 g of ethoxypropoxytristyrylphenol (block copolymer) and
10 g of N,N-dibutyl-C16-C18-carboxamide.

After addition has ended, the mixture is stirred at room temperature for a further 4 hours. In this way, a homogeneous solution is obtained.

Formulation Example 14

To produce the proper invention with the active ingredient bixafen, the following are first mixed at room temperature with stirring:
10 g of bixafen with
40 g of N,N-dimethyldecanamide and then with
10 g of aromatic hydrocarbon mixture, naphthalene-reduced,
10 g of 2-ethylhexanol propylene/ethylene glycol ether,
10 g of castor oil polyglycol ether ester,
5 g of ethoxypropoxytristyrylphenol (block copolymer) and
15 g of N,N-dibutyl-C16-C18-carboxamide.

After addition has ended, the mixture is stirred at room temperature for a further 4 hours. In this way, a homogeneous solution is obtained.

Formulation Example 15

To produce the proper invention with the active ingredient bixafen, the following are first mixed at room temperature with stirring:
10 g of bixafen with
40 g of N,N-dimethyldecanamide and then with
5 g of aromatic hydrocarbon mixture, naphthalene-reduced,
10 g of 2-ethylhexanol propylene/ethylene glycol ether,
10 g of castor oil polyglycol ether ester,
5 g of ethoxypropoxytristyrylphenol (block copolymer) and
20 g of N,N-dibutyl-C16-C18-carboxamide.

After addition has ended, the mixture is stirred at room temperature for a further 4 hours. In this way, a homogeneous solution is obtained.

Formulation Example 16

To produce the proper invention with the active ingredient isopyrazam, the following are first mixed at room temperature with stirring:
10 g of isopyrazam with
45 g of N,N-dimethyldecanamide and then with
10 g of aromatic hydrocarbon mixture, naphthalene-reduced,
10 g of 2-ethylhexanol propylene/ethylene glycol ether,
10 g of castor oil polyglycol ether ester,
5 g of ethoxypropoxytristyrylphenol (block copolymer) and
10 g of N,N-dibutyl-C16-C18-carboxamide.

After addition has ended, the mixture is stirred at room temperature for a further 4 hours. In this way, a homogeneous solution is obtained.

Formulation Example 17

To produce the proper invention with the active ingredient isopyrazam, the following are first mixed at room temperature with stirring:
10 g of isopyrazam with
40 g of N,N-dimethyldecanamide and then with
10 g of aromatic hydrocarbon mixture, naphthalene-reduced,
10 g of 2-ethylhexanol propylene/ethylene glycol ether,
10 g of castor oil polyglycol ether ester,
5 g of ethoxypropoxytristyrylphenol (block copolymer) and
15 g of N,N-dibutyl-C16-C18-carboxamide.

After addition has ended, the mixture is stirred at room temperature for a further 4 hours. In this way, a homogeneous solution is obtained.

Formulation Example 18

To produce the proper invention with the active ingredient fluxapyroxad, the following are first mixed at room temperature with stirring:
10 g of fluxapyroxad with
45 g of N,N-dimethyldecanamide and then with
10 g of aromatic hydrocarbon mixture, naphthalene-reduced,
10 g of 2-ethylhexanol propylene/ethylene glycol ether,
10 g of castor oil polyglycol ether ester,
5 g of ethoxypropoxytristyrylphenol (block copolymer) and
10 g of N,N-dibutyl-C16-C18-carboxamide.

After addition has ended, the mixture is stirred at room temperature for a further 4 hours. In this way, a homogeneous solution is obtained.

Formulation Example 19

To produce the proper invention with the active ingredient fluxapyroxad, the following are first mixed at room temperature with stirring:
10 g of fluxapyroxad with
40 g of N,N-dimethyldecanamide and then with
10 g of aromatic hydrocarbon mixture, naphthalene-reduced,
10 g of 2-ethylhexanol propylene/ethylene glycol ether,
10 g of castor oil polyglycol ether ester,
5 g of ethoxypropoxytristyrylphenol (block copolymer) and
15 g of N,N-dibutyl-C16-C18-carboxamide.

After addition has ended, the mixture is stirred at room temperature for a further 4 hours. In this way, a homogeneous solution is obtained.

Formulation Example 20

To produce the proper invention as a tankmix additive, the following are first mixed at room temperature with stirring:
50 g of N,N-dibutyl-C16-C18-carboxamide with
25 g of castor oil polyglycol ether ester and then with
25 g of benzyl alcohol.

After addition has ended, the mixture is stirred at room temperature for a further 2 hours. In this way, a homogeneous solution is obtained.

Formulation Example 21

To produce the proper invention with the active ingredient prothioconazole, the following are first mixed at room temperature with stirring:
20 g of prothioconazole with
44.9 g of N,N-dimethyldecanamide and then with
15 g of 2-ethylhexanol propylene/ethylene glycol ether,
10 g of castor oil polyglycol ether ester,
5 g of ethoxypropoxytristyrylphenol (block copolymer),
0.1 g of silicone antifoam emulsion and
5 g of N,N-dibutyl-C16-C18-carboxamide.

After addition has ended, the mixture is stirred at room temperature for a further 4 hours. In this way, a homogeneous solution is obtained.

The invention claimed is:

1. An agrochemical combination comprising a carboxamide of formula (I)

$$R^1\text{—CO—}NR^2R^3 \qquad (I)$$

in which
$R^1$ is $C_{16}$-$C_{18}$-alkyl or $C_{16}$-$C_{18}$-alkenyl and
$R^2$ is $C_4$-alkyl and
$R^3$ is $C_4$-alkyl
and prothioconazole,
wherein the carboxamide is capable of promoting penetration of the prothioconazole into a plant.

2. A combination as claimed in claim 1, in which a carboxamide of formula (I) is added to the prothioconazole as a tankmix additive.

3. An agrochemical formulation in the form of an emulsion concentrate or dispersion in oil, comprising:
prothioconazole and
at least one carboxamide of formula (I)

$$R^1\text{—CO—}NR^2R^3 \qquad (I)$$

in which
$R^1$ is $C_{16}$-$C_{18}$-alkyl or $C_{16}$-$C_{18}$-alkenyl and
$R^2$ is $C_4$-alkyl and
$R^3$ is $C_4$-alkyl, and
at least one solvent and/or oil.

4. The agrochemical formulation as claimed in claim 3, in which the content of the at least one carboxamide of formula (I) in the agrochemical formulation is from 1 to 50% by weight.

5. An agrochemical formulation comprising
15-35% by weight of prothioconazole,
25-45% by weight of N,N-dimethyldecanamide,
10-40% by weight of one or more emulsifiers,
0.01-1.0% by weight of defoamer, and
5-30% by weight of N,N-dibutyl-C16-C18-alkylcarboxamide and N,N-dibutyl-C16-C18-alkenylcarboxamide.

6. A method of promoting the penetration of prothioconazole into a plant comprising treating the plant with prothioconazole and a carboxamide of formula (I)

$$R1\text{-CO}\text{—}NR2R3 \qquad (I)$$

in which
R1 is C16-C18-alkyl or C16-C18-alkenyl,
R2 is C4-alkyl, and
R3 is C4-alkyl.

7. A combination as claimed in claim 1, wherein R2 and R3 are n-butyl.

8. A formulation as claimed in claim 3, wherein R2 and R3 are n-butyl.

9. A formulation as claimed in claim 4, wherein R2 and R3 are n-butyl.

10. A method as claimed in claim 6, wherein R2 and R3 are n-butyl.

11. A combination as claimed in claim 1, comprising a mixture of said carboxamides.

12. A formulation as claimed in claim 3, comprising a mixture of said carboxamides.

13. A formulation as claimed in claim 5, comprising a mixture of said carboxamides.

14. A method as claimed in claim 6, comprising applying a mixture of said carboxamides.

15. A combination as claimed in claim 1, comprising at least one carboxamide in which R1 is C16-C18-alkyl and at least one carboxamide in which R1 is C16-C18-alkenyl.

16. A formulation as claimed in claim 3, comprising at least one carboxamide in which R1 is C16-C18-alkyl and at least one carboxamide in which R1 is C16-C18-alkenyl.

17. A formulation as claimed in claim 5, comprising at least one carboxamide in which R1 is C16-C18-alkyl and at least one carboxamide in which R1 is C16-C18-alkenyl.

18. A method as claimed in claim 6, comprising at least one carboxamide in which R1 is C16-C18-alkyl and at least one carboxamide in which R1 is C16-C18-alkenyl.

* * * * *